United States Patent
Leskiw

(10) Patent No.: US 10,444,353 B2
(45) Date of Patent: Oct. 15, 2019

(54) IMAGING SYSTEM AND METHOD USING IMPROVED MODULATED EXCITATION

(71) Applicant: 8517401 Canada Inc., Ottawa (CA)

(72) Inventor: Christopher John Leskiw, Calgary (CA)

(73) Assignee: 8517401 Canada Inc., Ottawa, ON (CA)

( * ) Notice: Subject to any disclaimer, the term of this patent is extended or adjusted under 35 U.S.C. 154(b) by 0 days.

(21) Appl. No.: 15/822,038

(22) Filed: Nov. 24, 2017

(65) Prior Publication Data

US 2018/0149746 A1 May 31, 2018

Related U.S. Application Data

(60) Provisional application No. 62/426,380, filed on Nov. 25, 2016.

(51) Int. Cl.
| | | |
|---|---|---|
| *G01S 15/89* | (2006.01) | |
| *H04L 27/38* | (2006.01) | |
| *H04B 1/709* | (2011.01) | |
| *H04L 27/36* | (2006.01) | |
| *G01S 7/52* | (2006.01) | |

(Continued)

(52) U.S. Cl.
CPC ...... *G01S 15/8977* (2013.01); *G01S 7/52019* (2013.01); *G01S 7/52026* (2013.01); *G01S 7/52031* (2013.01); *G01S 7/52046* (2013.01); *G01S 7/52093* (2013.01); *G01S 7/531* (2013.01); *G01S 15/8906* (2013.01); *G01S 15/8913* (2013.01); *G01S 15/8959* (2013.01); *H04B 1/709* (2013.01); *H04L 27/364* (2013.01); *H04L 27/38* (2013.01); *A61B 8/52* (2013.01); *G06F 19/321* (2013.01); *G16H 50/50* (2018.01);
(Continued)

(58) Field of Classification Search
CPC ........ H04B 1/709; H04B 1/7093; H04B 3/30; H04B 2201/70751; H04B 2201/70716; H04L 27/10; H04L 27/18; H04L 27/26; H04L 27/2601; H04L 27/364; H04L 27/366; H04L 27/38; H04J 13/0033; G01S 7/52019; G01S 7/52026; G01S 7/52031; G01S 7/52046; G01S 7/52093; G01S 7/531; G01S 15/8906; G01S 15/8913; G01S 15/8959; G01S 15/8977; G06F 19/321; G16H 50/50; A16B 8/52
USPC ....... 375/141, 142, 219, 220, 222, 257, 260, 375/279, 308, 329, 343; 455/500, 501, 455/67.11, 67.13, 70, 73, 88
See application file for complete search history.

(56) References Cited

U.S. PATENT DOCUMENTS

| | | | | |
|---|---|---|---|---|
| 5,278,992 | A | * | 1/1994 | Su ............... H03M 5/145 455/127.2 |
| 5,559,788 | A | * | 9/1996 | Zscheile, Jr. ......... H04J 13/00 370/206 |

(Continued)

*Primary Examiner* — Young T Tse
(74) *Attorney, Agent, or Firm* — Gowling WLG (Canada) LLP

(57) ABSTRACT

An imaging system that utilizes deterministic bit sequences modulated onto an in-phase component of a carrier frequency and continuously transmitted via a transducer and received for imaging a medium and/or environment is provided. The received signal is demodulated by an in-phase demodulator and a quadrature demodulator and the demodulated components are processed to provide a spatial mapping of a medium or environment being imaged.

22 Claims, 27 Drawing Sheets

(51) Int. Cl.
*G01S 7/531* (2006.01)
*A61B 8/08* (2006.01)
*H04J 13/00* (2011.01)
*G06F 19/00* (2018.01)
*G16H 50/50* (2018.01)

(52) U.S. Cl.
CPC ............. *H04B 2201/70715* (2013.01); *H04B 2201/70716* (2013.01); *H04J 13/0033* (2013.01)

(56) References Cited

U.S. PATENT DOCUMENTS

| | | | | |
|---|---|---|---|---|
| 5,623,485 | A * | 4/1997 | Bi | .......................... H04B 1/707 370/209 |
| 2012/0232399 | A1* | 9/2012 | Lee | ..................... G01S 7/52046 600/453 |
| 2015/0260835 | A1* | 9/2015 | Widmer | .................. G01S 13/04 342/27 |
| 2015/0288546 | A1* | 10/2015 | Kwon | ................... H04L 25/061 375/319 |

* cited by examiner

IMAGING SYSTEM AND METHOD USING IMPROVED MODULATED EXCITATION

CROSS-REFERENCE TO RELATED APPLICATIONS

This application claims priority from U.S. Provisional Application No. 62/426,380 filed Nov. 25, 2016, the entirety of which is hereby incorporated by reference for all purposes.

TECHNICAL FIELD

The current application relates to imaging systems and in particular to an imaging system to determine properties of a medium or environment or targets contained therein using modulated excitation.

BACKGROUND

In conventional non-destructive imaging systems, short pulse duration is critical for resolving anomalies existing in a test area. If the pulse duration is too long, near surface anomalies are eclipsed while the receiver waits for the transmit event to complete. Similarly, the ability for the system to distinguish between two or more anomalies along the same trajectory is dependent on a sufficiently narrow pulse. Unfortunately reducing pulse duration is not without its consequences. A narrow pulse has less detectable energy for the test equipment to reliably recover from the test site. The problem worsens as the excitation beam diverges and returns lower recoverable energy levels in proportion to increasing scan depth, lowering the SNR. This divergence over distance also increases the probability of exciting off-path reflection sources. Inadequate lateral scan line resolution can yield non-existent irregularities or ghosts that present themselves as actual in-line anomalies in regions where multiple reflection paths interact outside the path of interest and return to the receiver. A compromise must be reached that satisfies the SNR limits of the test equipment while attaining the desired scan resolution.

At present a partial solution will employ pulse compression techniques and/or array focusing to achieve the higher energy levels as with a longer pulse while partitioning the energy such that it maintains the resolution of a short pulse. However pulse compression does not unveil the anomalies existing in the near surface blind region created by the longer transmit event. A further drawback is the increased complexity at high voltage levels makes implementations more costly. At present resolutions are improved by changing to a probe that uses a smaller per-element excitation surface area whether in a single element device or a multi-element phased array. Therefore there is a need for an improved imaging system and method using improved modulated excitation.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
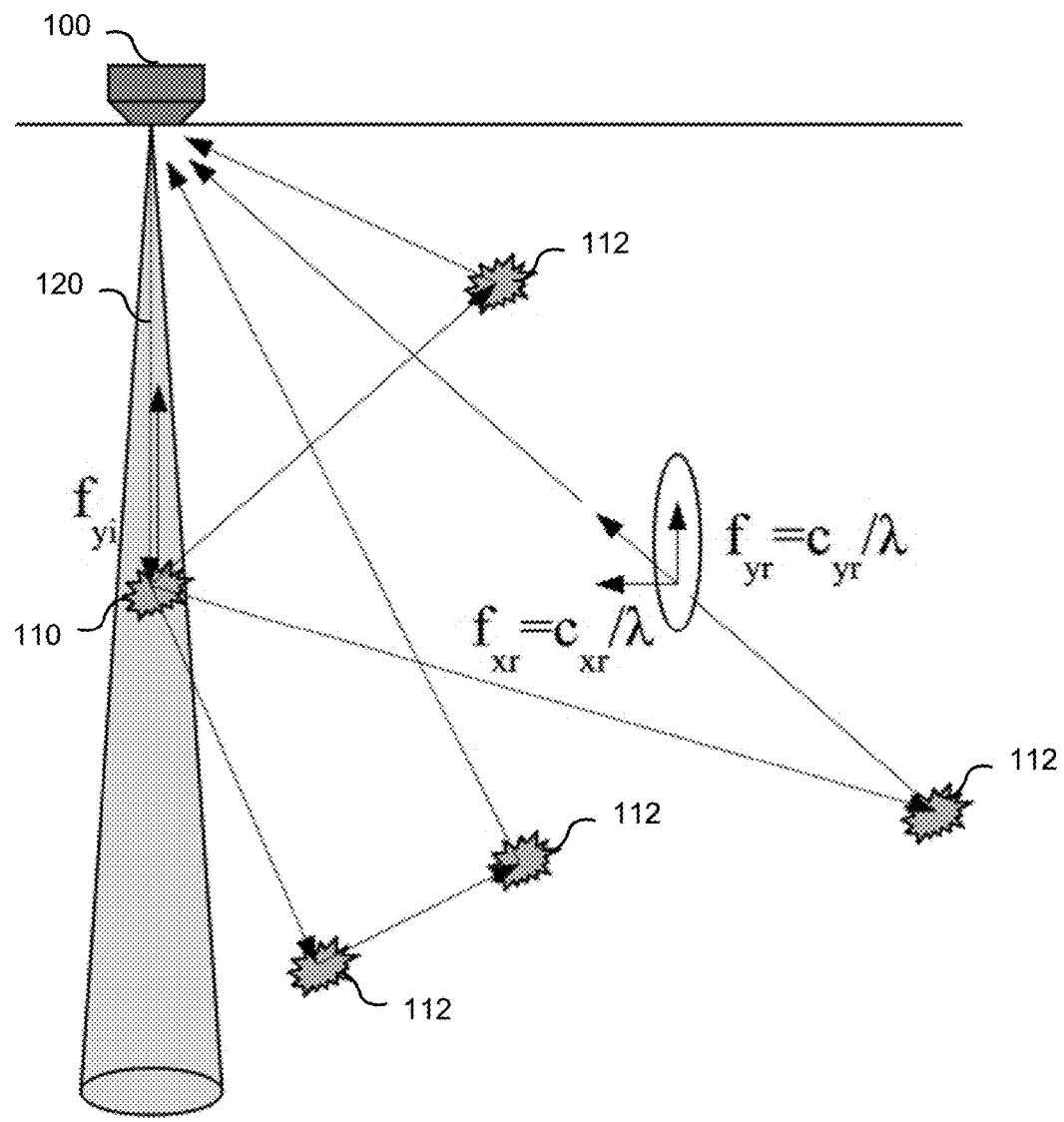
FIG. 1 depicts frequency components of off-angle arrivals.

In accordance with the present disclosure there is provided an imaging system comprising: a deterministic bit sequence generator for generating a transmit sequence; an in-phase modulator for modulating the generated transmit sequence with a transmit carrier frequency to generate an imaging waveform; a transducer for transmitting the generated imaging waveform into a medium or environment being imaged and receiving a response signal; an in-phase demodulator for demodulating an in-phase component of the response signal; a quadrature demodulator for demodulating a quadrature phase component of the response signal; and a controller for processing the demodulated in-phase component of the response signal and the quadrature phase component of the response signal to create a spatial mapping of properties of the medium or environment being imaged.

In accordance with yet another aspect of the present disclosure there is provided A method of imaging a medium, the method comprising: generating a deterministic bit sequence by a processor; performing in-phase modulation of the generated deterministic bit sequence to generate an imaging waveform; transmitting by a transducer the imaging waveform into the medium being imaged; receiving a response signal by the transducer associated reflected from the medium or environment; performing in-phase demodulation of an in-phase component of the response signal; performing quadrature phase demodulation of the response signal; and processing by the processor the demodulated in-phase component of the response signal and the quadrature phase component of the response signal to create a spatial mapping of properties of the medium being imaged.

The invention will now be described in detail with reference to various embodiments thereof as illustrated in the accompanying drawings. Specific details are set forth in order to provide a thorough understanding of the invention. It will be apparent to one skilled in the art that the invention may be practiced without using some of the implementation details set forth herein. It should also be understood that well known operations have not been described in detail in order to not unnecessarily obscure the invention. Embodiments are described below, by way of example only, with reference to FIGS. 1-27.

An imaging technique using indefinite binary modulation of deterministic signature excitation waveforms for non-destructive testing may be used to decouple the pulse duration and resolution compromise, even if available power is fixed. The technique as described further herein can be used to reduce the outgoing excitation pulse amplitude driving a conventional transducer probe from hundreds of volts to voltages on the order of 1Vp-p while maintaining the scan resolution and improving SNR by amounts in excess of 30 dB. The technique may also be successfully used in resolving near surface artifacts despite arbitrarily long excitations as transmission and signal recovery occurs simultaneously. Lateral resolution may also be effectively improved and ghosting reduced with the same transducer probe when the excitation is modulated and demodulated appropriately. The recovered system response from a binary modulation technique is able to discriminate against off-path reflection sources that would otherwise act like ghosts and appear as in-line irregularities. Furthermore the receiving beam profile can be steered to identify the angle from where a ghost anomaly is sourced. Even when using a conventional transducer, the imaging techniques described herein allows the effective profile of an imaging beam to be narrowed, reducing foreign anomalies that previously degraded the results. Further still, the technique can improve SNR despite lower excitation amplitudes.

Active image acquisition is a trade-off between many factors including available signal power, allowable signal power, medium bandwidth and image frame rate. Excitation signals derived from short codes or modulated pulses is an area of much research to improve performance. The techniques described herein uses binary modulated, such as for example Kasami transmit sequences to identify scatterer parameters and locate heterogeneities or discontinuities. Kasami sequences are binary sequences of length $2^N-1$ where N is an even integer. Kasami sequences have good cross-correlation values approaching the Welch lower bound. Although Kasami sequence is described other continuous deterministically coded sequences may be utilized. For example a set of pseudo-noise (PN) sequences can be utilized that have an autocorrelation result that approximates an impulse function and have a cross correlation result with an optimum lower bound (i.e. the cross correlation result is deterministic and satisfies the Welch lower bound). The use of long transmit sequences as compared to traditional short duration pulses provides a means of increasing signal-to-noise ratio despite a fixed amount of transmit power.

The current technique may address more than one issue related to the target ranging and imaging problem. The system uses information from a continuous, modulated, illuminating imaging beam on two carrier phases in contrast to short, unmodulated, high energy pulses for the recovery of the locations of scatterers normally undetectable with shorter excitations of the same amplitude. Further, the system provides concurrent transmitting and receiving of multiple scan lines in the same environment. This ability may be achieved by employing mathematically deterministic sequences with optimal orthogonality from the Kasami set such that multiple independent scan lines are able to be de-correlated and recovered. Yet another feature is multiple scan area parameter identification from demodulated in-phase and quadrature versions of the recovered sequences. These provide linearly independent information related to wave affecting parameters of scatterers. The techniques described herein can be implemented with low cost architectures.

As described further below, the technique is verified by an analytical model that relates the cross-correlation result of long deterministic sequences and recovered information to locations and physical parameter values. Mathematical and computer simulation shows that with binary modulated, Kasami transmit sequences, even if sustained indefinitely, the system can recover multiple wave influencing property values of scatterers, and detect internal interfaces of objects despite interference from foreign, concurrent imaging beams and medium heterogeneity.

For the problem of mapping the location of heterogeneities in an actively excited medium, an impulse response method is applied to the medium or environment, and then mathematically to the wave equation. The resulting equation is in terms of unknown medium parameters like wave velocity and spatial density. Measured data from the imposed excitation and the recorded responses are inverted to create a spatial map of the medium's properties. The spatial map is then verified against the actual system by applying the imposed excitation to the model and comparing the predicted results to the actual recorded data. New excitation methods that are being researched to improve resolution and frame rate include pulse compression techniques like frequency sweeps and bursts of coded signals. Research is also ongoing for Green's function extraction from cross-correlations of random fluctuations within the media of interest. Extracting the Green's function or impulse response from cross-correlations even for a one dimensional case suffers from multiple internal reflections which impairs immediate mapping of the impulse response data to actual medium parameters. Continuous deterministically coded sequences provide an opportunity to recover multiple impulse responses simultaneously.

A system is described further herein that performs any combination of the following: target imaging, physical parameter identification, and target location with modulated excitation that uses long, mathematically deterministic sequences transmitted on one phase vector with recovery on multiple orthogonal phase vectors. The resultant scanning beam can be narrower, steerable, permit shallow scans, permit scans at extreme wave velocities and excite the medium with power levels 100× less than current conventional methods such as ultrasonics.

This system improves upon other methods that use short pulses, compressed pulses, Barker sequences, Hadamard sequences and other pseudo-random type sequences as Kasami sequences are employed and provide an impulse-like autocorrelation result, and have fixed optimal cross correlation results (i.e. the cross correlation result is deterministic and satisfies the Welch lower bound). Issues that impair pseudo-random signals like those mentioned above include limited length as in Barker sequences, do not have asynchronous cross correlation results that meet the Welch lower bound as in Hadamard sequences, limit the number of concurrent orthogonal sequences as in Golay sequences and/or have difficult to predict cross correlation values as is the case for Gold sequences.

The technique makes use of binary modulation on a specific carrier frequency and phase while demodulating on multiple phases and potentially differing frequencies. There is a natural filtering of off-angle arrivals due to an apparent shift in frequency from the frequency that was used to deliver the illuminating waveform. Consider the illustration in FIG. 1, energy is directed downward and is then scattered by an anomaly 110 below the transducer/antenna 100. When the energy interacts with an anomaly 110, the energy is reflected in typically unpredictable directions potentially exciting off-angle anomalies 112 that may in turn reflect the energy back towards the transducer 100. Accurate imaging requires the system to reliably recreate the environment along the scan line 120. The recreation is impaired when the transducer 100 cannot distinguish returning energy from reflectors 110 along the scan line 120 from those arriving from outside the desired scan line 120. The off-angle arrivals appear to have different frequency components when the detector is projecting in a different direction and therefore can be reliably detected as off-angle components. The carrier frequency of the y component of the off-angle excitation signal $f_{yr}$ will be different than the incidence excitation carrier frequency $f_{yi}$.

Figure 2:
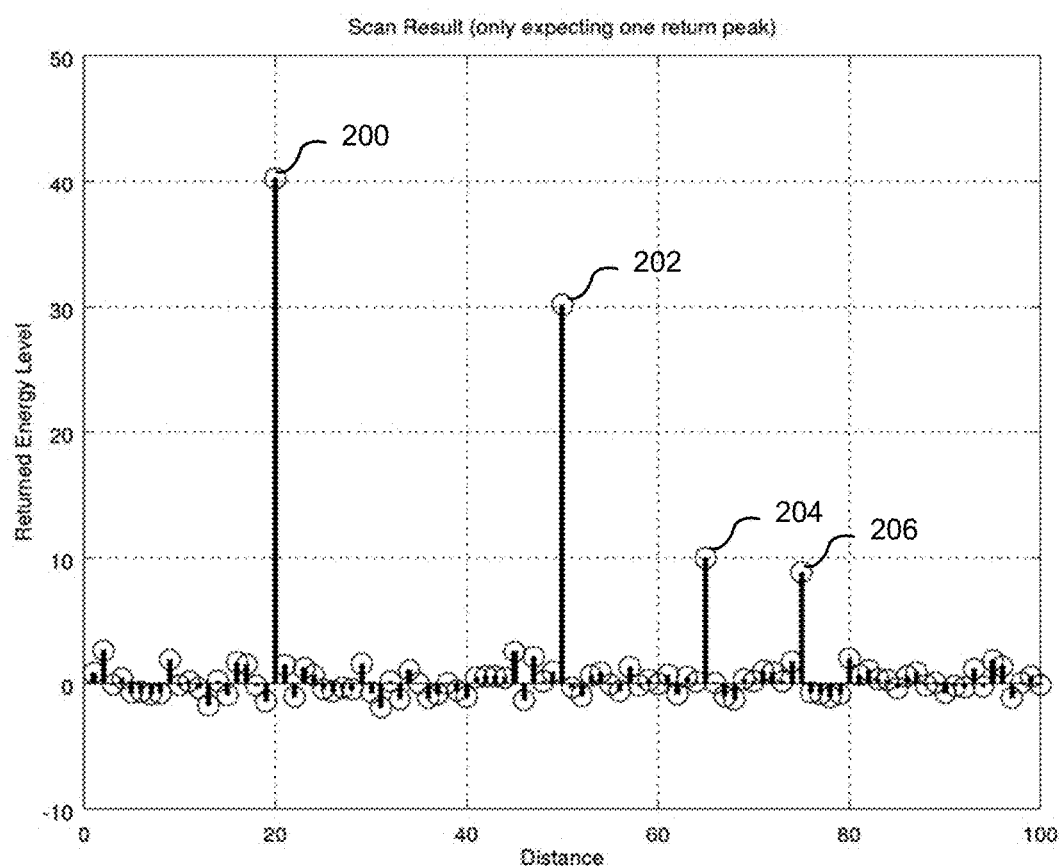
FIG. 2 depicts results from components of off-angle arrivals.

As shown in FIG. 2, under ideal circumstances the result trace resulting from the example depicted in FIG. 1 would contain only one main peak 200, locating the effect of only one reflector. For reasons made worse by divergence of the scanning beam, more energy is available for off-angle reflectors and the energy returned by those reflectors can show up in the scan result as multiple peaks 202, 204, 206 as depicted in FIG. 2.

Figure 3:
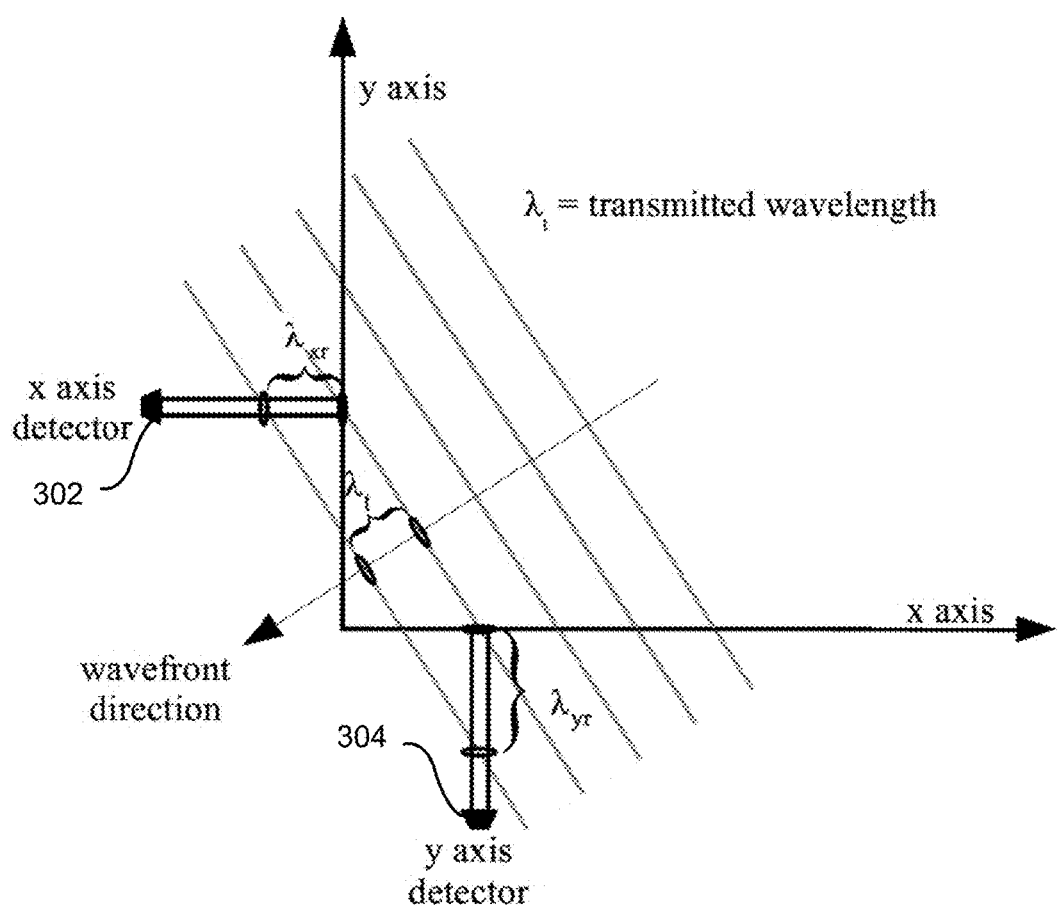
FIG. 3 depicts isolating components of off-angle arrivals.

FIG. 3 further illustrates the different distances between wavefronts for an off-angle arrival that is split into two orthogonal spatial components. It illustrates a detector 302 at the end of a horizontal (x axis) opening and a detector 304 at the end of a vertical (y axis) opening. The different timings of the wavefronts reaching each detector is shown. The resulting frequency apparent to the x axis detector is different from the frequency seen by the y axis detector which is also different from the transmitted frequency in the direction of the wavefront.

Figure 4:
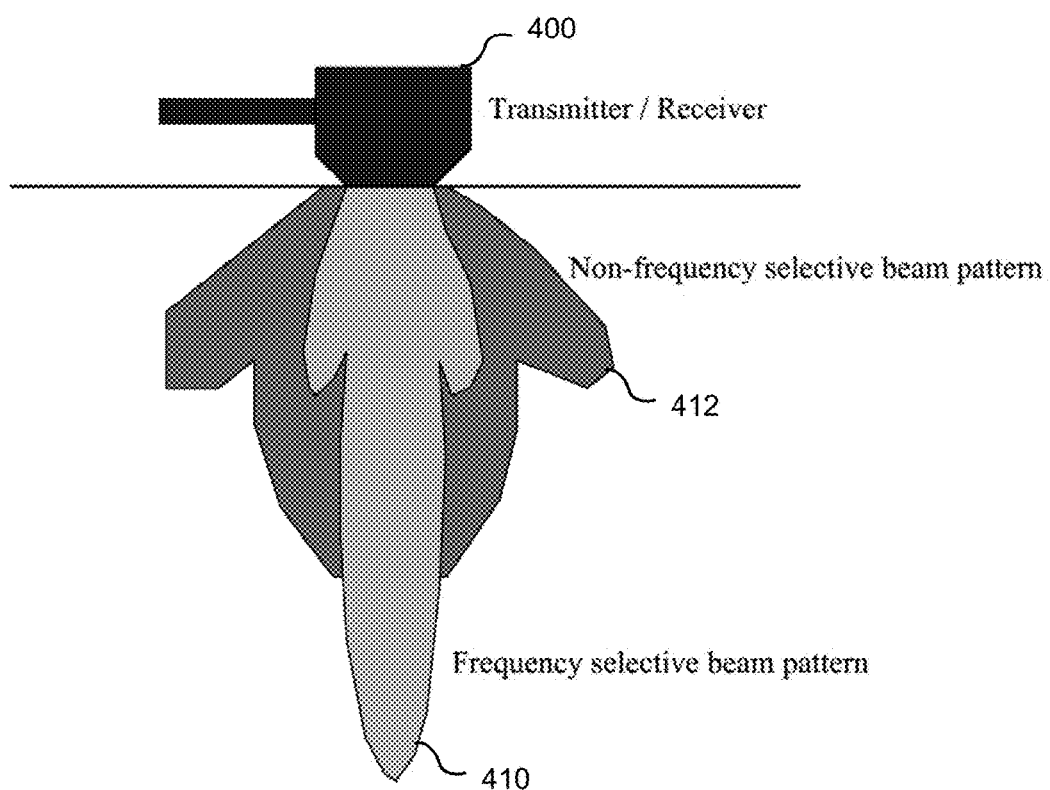
FIG. 4 depicts frequency selective beam narrowing.

When a system 400 is selective of specific frequencies the effective radiation sensitivity pattern 410 is more directive as shown in FIG. 4. In conventional, non-frequency selective applications, the receiver recovers energy from a wider range of frequencies 412 and therefore a range of angles resulting in a beam pattern much wider than a frequency selective one.

Figure 5:
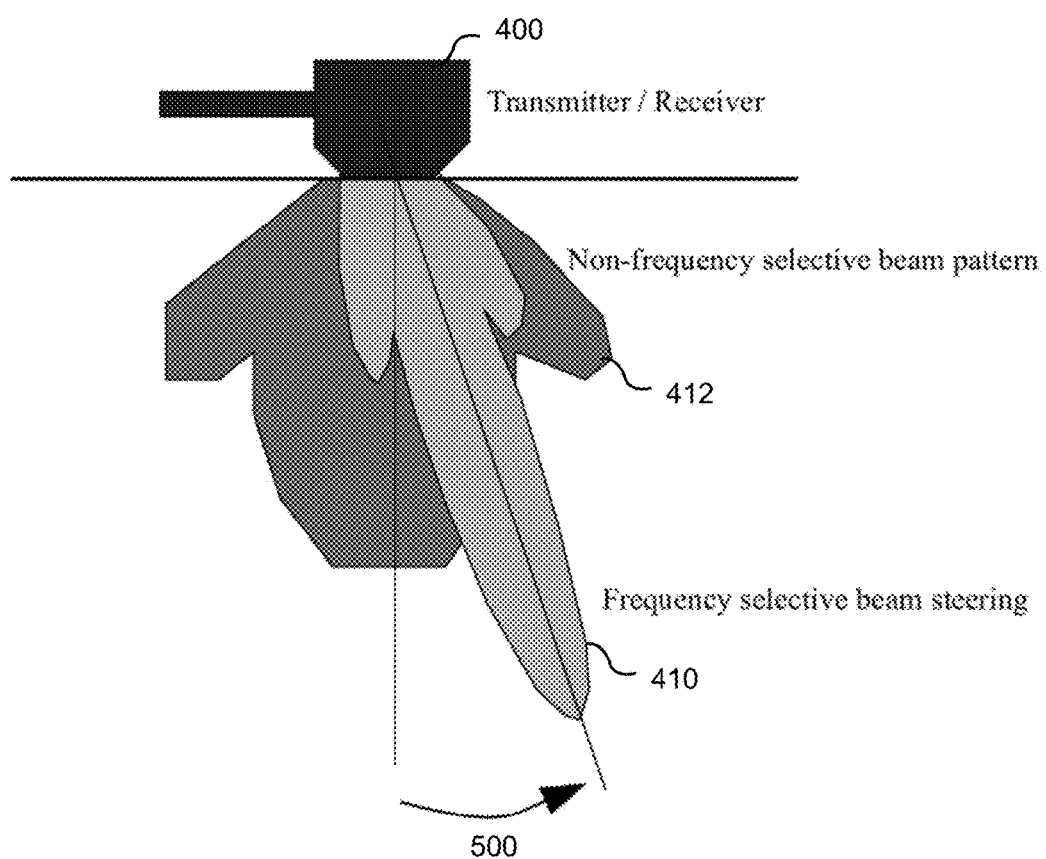
FIG. 5 depicts frequency selective beam steering.

Taking advantage of the apparent difference in frequencies for x and y directional components allows for effective beam steering. Therefore not only can scan lines be more immune to off-angle arrivals, but as illustrated in FIG. 5 the scan line angle 500 can be tuned to image over a variety of scan angles without physically moving the transmitter/receiver or adding more transducer elements. The direction of the beam is proportional to the difference between the transmitted and receive frequencies chosen for transmit and receive.

Figure 6:
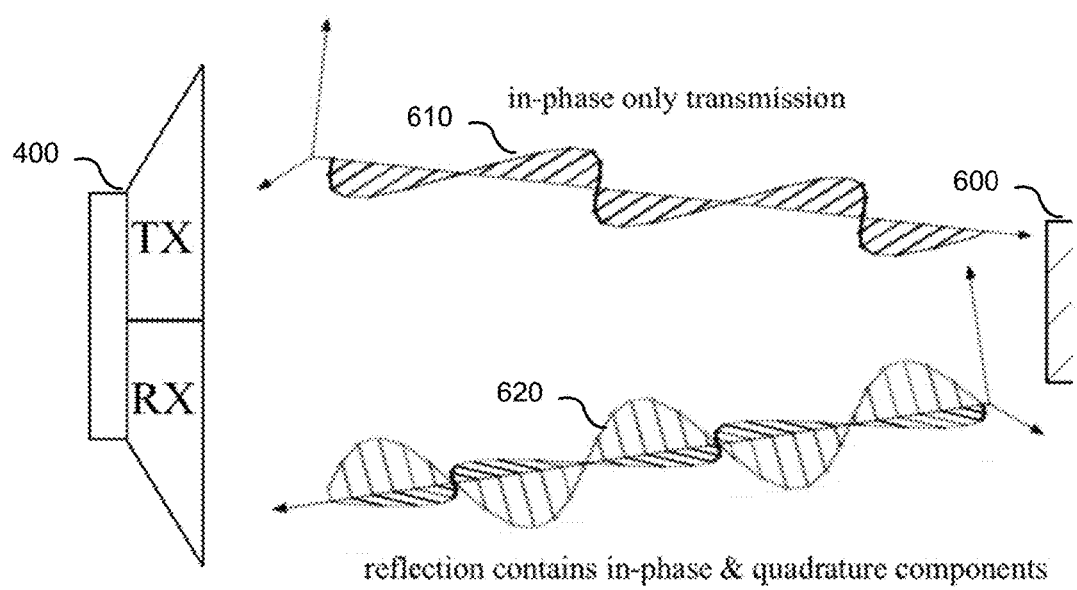
FIG. 6 depicts the energy transmitted on the in-phase component only, collected from in-phase and quadrature phase components as anomalies reflect energy on both

Energy encoded by a Kasami or other PN sequence is modulated on to a specific carrier frequency. This signal is purposely transmitted 610 only on one phase and a null signal occupies the quadrature phase. Then when an anomaly 600 is encountered the energy is reflected back 620 towards the transmitter 400, with amounts uniquely distributed in the quadrature and in-phase components as illustrated in FIG. 6. The scatter's properties will reflect different amounts of the received energy onto phases that are proportional to specific properties of the scatterer. In other words unique wave affecting properties of the scatter (density and wave velocity for example) will allocate the energy in unique proportions onto the in-phase and quadrature phases. So long as the transmission continues long enough to be reliably detected, energy measurements can be taken of the power levels received in each component and then processed to determine the location of the anomaly and/or its properties.

Normally, as is the case for ultrasonics, the sample rate of the equipment is high enough that an accurate measurement can be made of the time between the outgoing and returning pulse or excitation signal. By taking measurements of power levels that persist over time the normally insufficient sample rates for information traveling at or near the speed of light that prohibits time of flight measurements can instead be used to measure the power in each phase. If a relatively shallow measurement is attempted with electromagnetic waves, the sample rates of modern equipment is not high enough to make an accurate measurement of the time between the outgoing and incoming excitations. What does persist long enough to take an accurate measurement is the amount of energy recoverable in each phase as long as the transmission is long enough to make such a measurement. In other words the measurements required to determine the power level of energy in each phase can be accomplished with conventional sampling rates and does not depend on timing differences because the timing distance is not a factor in the power calculation.

It is impractical to send the sequence in its baseband form. Graceful delivery of the user's baseband digital sequence is accomplished by modulating the signal to a frequency band acceptable to the medium and the transmitting and receiving equipment. The form of the bandpass signal applied by the system is:

$$b(t) = \sqrt{\frac{2\epsilon}{T}} \cos\left(\omega_0 t + \frac{\pi}{2}(1 - \kappa(t))\right) \quad (1)$$

Where $\epsilon$ is a constant representing the energy per bit, $\kappa(t)$ contains the bits in the mathematically determined sequence, $\omega_0$ is the center radian frequency of the up-converted spectrum and T is the bit period. Detection of reflected energy or reflected versions of the transmitted signal requires combining in-phase and quadrature phase components that are generated due to the unknown asynchronous reflected transmissions arriving out of phase with the demodulator. In conventional communication systems this is referred to as I Q imbalance. In the current imaging system no information is transmitted in quadrature with the carrier. However due to the random asynchronous nature of mediums and targets being imaged the reflections return usually with unpredictable amplitude and phase alterations. Therefore it is equally likely that information demodulated to baseband by a modulator with 0 degrees phase shift is less effective than using a demodulator with a π/2 degrees (i.e. in quadrature) phase shift. Fortunately in this implementation information is only transmitted using the in-phase carrier. Therefore there is no leakage of information to another phase that would corrupt information native to that carrier as is the problem when unique information is transmitted on the quadrature carrier. The amount of correlation of the signature sequence with the received in phase component, when combined with the amount of correlation found in the quadrature component provides all the information to fully account for the complex representation (real and imaginary components) of the system response. In a real system where signals are sampled to work in a discrete time system, each signature sequence bit is resampled to a rate that accommodates sampling by a modulation waveform. The modulation waveform itself requires a number of samples to define the carrier waveform over. The sequence's rate through the medium is determined by:

$$\kappa_g = \text{samples per code bit} \times T_g = \text{seconds/code bit}. \quad (2)$$

Distance per bit can be calculated with $\kappa_s \times c_0$. This permits the translation of a sequence offset to a distance or vice versa. Index values into the recovered system response array represents the same distance change. Therefore a discrete component of the system response array not only represents a component of the impulse response of the medium but also implies the location of the discontinuity that is responsible for that part of the overall system response.

Allowing for multiple concurrent scans in the same environment is achieved by using sequences with favorable orthogonality resulting in attractive cross-correlation properties such that foreign scan's energy can be decorrelated out of the desired scan's signal. The process of decorrelation reveals the medium's response to the incident excitation. Recovery of the parameters that define a scatterer within the scanner's range is a three step process. First the received signal from the receiver requires demodulation into orthogonal carriers. Secondly the process performs the multi-user removal steps which result in unique system responses for each of the concurrent scanlines. Allowing for multiple concurrent scans in the same environment is achieved by using sequences with favorable orthogonality resulting in attractive cross-correlation properties such that foreign scan's energy can be decorrelated out of the desired scan's signal. The process of decorrelation reveals the medium's response to the incident excitation. The system response is applied to the wave equation and inverted to finally retrieve the physical parameters (e.g. wave velocity, density, etc.) of the scatterers in the system.

Figure 7:
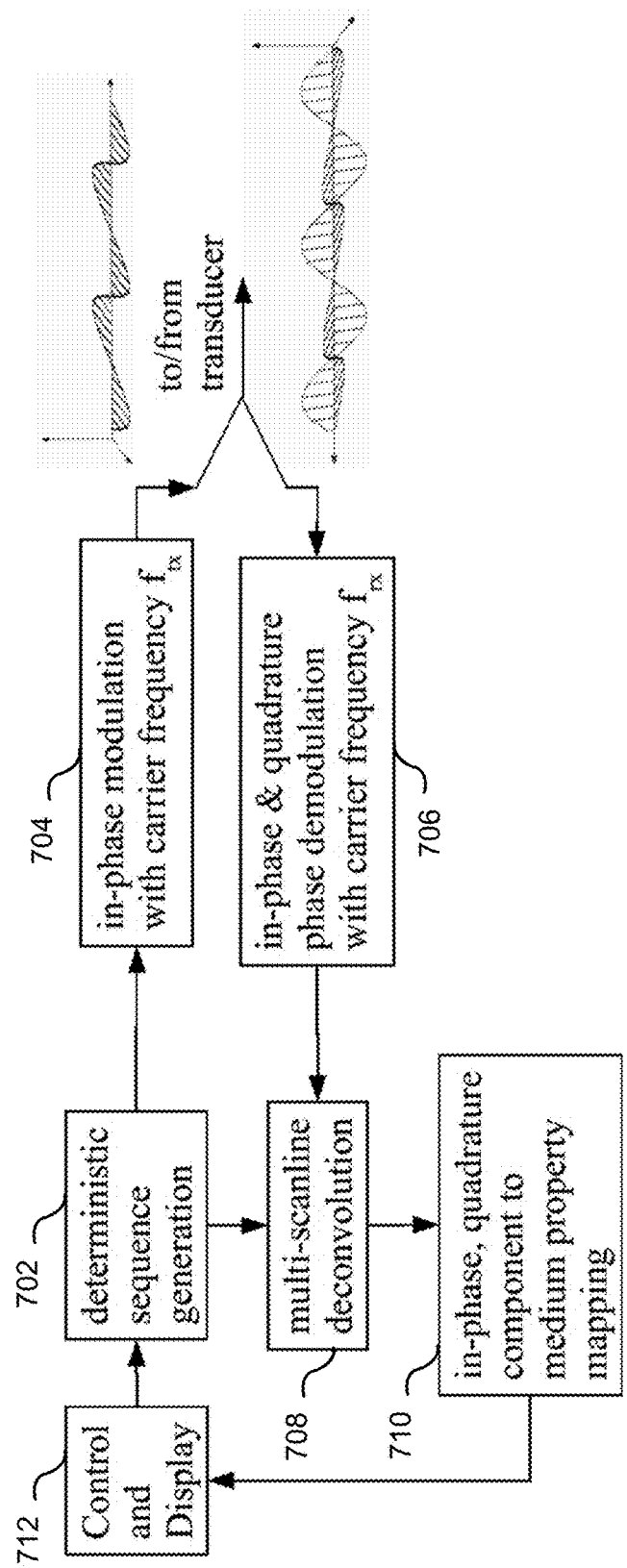
FIG. 7 depicts a system overview.

Features of the system include:
1. An imaging process that moves conventional imaging from a pulse-echo scheme to that of a continuous, modulated, illuminating beam—This contribution provides another method of delivering and recovering energy within a medium or environment for the purpose of imaging areas of interest, allowing for increased SNR despite fixed output power;
2. Extension of the method to multiple coexisting continuous scanlines in the same medium—the nature of the longer mathematically deterministic sequences lend themselves to multi-user imaging methods as the required signals are pseudo-orthogonal;
3. Demonstrated parameter identification advantages based on modulated mathematically determined sequences and demodulated in-phase and quadrature phase components—density and wave velocity values, for example, each affect the relative phase amplitude relationship between the in-phase and quadrature system response independently, which assists in their identification;
4. Effective beam narrowing—Modulation and demodulation of the excitation by a specific carrier inherently filters out off-angle reflections as the wave velocity component in the direction of the probe presents as a waveform with a center frequency different than that used for transmission;
5. Effective beam steering—Modulation at one frequency and careful demodulation at an offset frequency to the excitation inherently steers the optimal receiving direction off-angle to the incident direction;
6. Increased immunity to heterogeneous environments—Modulation at one frequency and careful demodulation with the same frequency to the excitation inherently improves performance in heterogeneous environments as off-angle arrivals from diverse parts of the medium are orthogonal in frequency to the incident excitation direction;
7. Overcoming the challenge of measuring the time delay for outgoing and reflected versions of an EM wave traveling at or near the speed of light—Measurement of the distance is related to a phase difference that presents as a power component in the quadrature component of the demodulated recovered signals;
8. Overcoming equipment instantaneous power limitations in order to improve SNR with sequence length—The instantaneous power limit of equipment can be overcome by using a longer sequence. Normally this has diminishing returns for other coded imaging schemes but here, because the beam is narrower due to modulation on a carrier, this system is more immune from environment/medium heterogeneity causing off-angle noise An embodiment of the system is depicted in FIG. 7. A PN deterministic sequence is generated 702 and is in-phase modulated with carrier frequency $f_{tx}$ 704 which is provided to the transducer. The in-phase and quadrature phase with carrier frequency $f_{rx}$ 706 are received by the transducer from the medium or environment and demodulated. Multi-scanline deconvolution is performed 708 with the received signal and the deterministic sequence that was generated. The in-phase and quadrature component is then mapped to the medium property to determine distance and composition 710 which can then be displayed 712.

Verification

The system described above is further described mathematically and shown feasible in simulations with a virtual implementation. For simple scatterers, the predictions given for the phase effects caused by wave influencing parameters matched simulation results. For the imaging of objects, the continuous Kasami sequences were able to detect the interfaces despite another Kasami sequence operating simultaneously. The results verified the use of a continuous beam for imaging an environment while other users were operating in the same area. In addition to cases where properties of a scatter are identified, work is undertaken in cases where more than one transmitter and more than one receiver are operating in the same area and at the same time and frequency. In all cases binary phase shift keying is the modulation process used to deliver the baseband signals to the medium at frequencies most applicable to the transmission properties of the simulation model.

The verification exercise uses an ultrasonic model that takes the result from the cross-correlation of a long mathematically deterministic input sequence and a recovered signal to determine the properties of an acoustically excited medium. The process is applicable to other types of imaging environments and wave types such as EM radiation. Starting from the analytical description of the wave-field that is influenced by heterogeneities in the medium and bridging the gap to connect it with the result of the correlation was done through the scatter's influence on wave speed and density.

System Description

The analytical system for predicting and verifying the concept is developed from the underlying physical equations for scattering. Development starts from the fundamental equation of scattering theory, known as the Lippmann-Schwinger equation shown here in operator form:

$$\Psi = G - G_0 = G_0 V G. \tag{3}$$

Here $\Psi$ is not an operator but represents the scattered field. The equation is rearranged to isolate the heterogeneous Green Function G:

$$G = G_0 + G_0 V G. \tag{4}$$

The Green's method solution written in differential operator form is:

$$LG = -\delta(x - x_s). \tag{5}$$

The differential operator L for a mechanical wave, as in ultrasonics for example, is defined as:

$$L = \frac{\omega^2}{k} + \nabla \cdot \left(\frac{1}{\rho} \nabla\right). \tag{6}$$

The perturbation operator V is defined as the difference between the actual medium parameters and reference medium parameters. The reference medium is defined with the homogeneous medium parameters $\kappa_0$ and $\rho_0$:

$$L_0 = \frac{\omega^2}{k_0} + \nabla \cdot \left(\frac{1}{\rho_0} \nabla\right) \tag{7}$$

therefore the operator V, being the result of $L-L_0$ has the expanded form:

$$V = \omega^2 \left(\frac{1}{\kappa} - \frac{1}{\kappa_0}\right) + \nabla \cdot \left[\left(\frac{1}{\rho} - \frac{1}{\rho_0}\right) \nabla\right]. \tag{8}$$

The equation $G = G_0 + G_0 V G$ has an equivalent infinite sum:

$$G = \frac{G_0}{1 - VG_0} = \sum_{n=0}^{\infty} G_0 (VG_0)^n. \tag{9}$$

Therefore the heterogeneous Green's function can be rewritten in terms of the known components $G_0$ and the perturbation operator V:

$$G = G_0 + G_0 V G_0 + G_0 V G_0 V G_0 + \ldots \tag{10}$$

Noting that the later terms of equation (10) accommodate the multiple internal reflections. The primary component involves the incident wave and the primary reflection:

$$G = G_0 + G_0 V G_0. \tag{11}$$

Employing straightforward superposition equation (11) is reworked to address multiple discrete scatterers:

$$G(x_m, x_s) = G_0(x_m, x_s) + \Sigma_{n=1}^{N} G_0(x_m, x_s) V(x_n) G_0(x_m, x_n) \tag{12}$$

where $x_n$, $x_s$ and $x_m$ denote the scatter, source and measurement locations respectively. Knowing that the reflected energy is sourced over the cross sectional area $\Omega_n$ of the scatterer, the returning energy is integrated over that cross sectional area:

$$G(x_m, x_s) = G_0(x_m, x_s) + \Sigma_{n=1}^{N} G_0(x_n, x_s) V(x_n) \int_{\Omega_n} G_0(x_m, x') d\Omega(x'). \tag{13}$$

If the domain covered by N pixels is restricted (by beam-forming for example) to isolate the problem to one of one dimension such that a domain $\Omega_{N \times M} \in \Omega_Z$, then the impulse response can be related to the medium in a more straightforward manner, replacing the task of accommodating energy arriving from all directions all at once. To clarify, the domain $\Omega_Z$ is a subsection of a two dimensional domain, effectively a one dimensional domain along some arbitrary axis. Other directions and multiple dimensions can be assembled from the composite of multiple linear measurements. The channel response i.e. the Green's function representing the medium is equivalent along a linear domain, and for this one dimensional case equation (13) can be rewritten as:

$$G_z = (x_m, x_s) = G_0(x_m, x_s) + \Sigma_{n=1}^{N} G_0(x_n, x_s) V(x_n) \int_{\Omega_n} G_0(x_m, x') d\Omega(x'). \tag{14}$$

Figure 8:
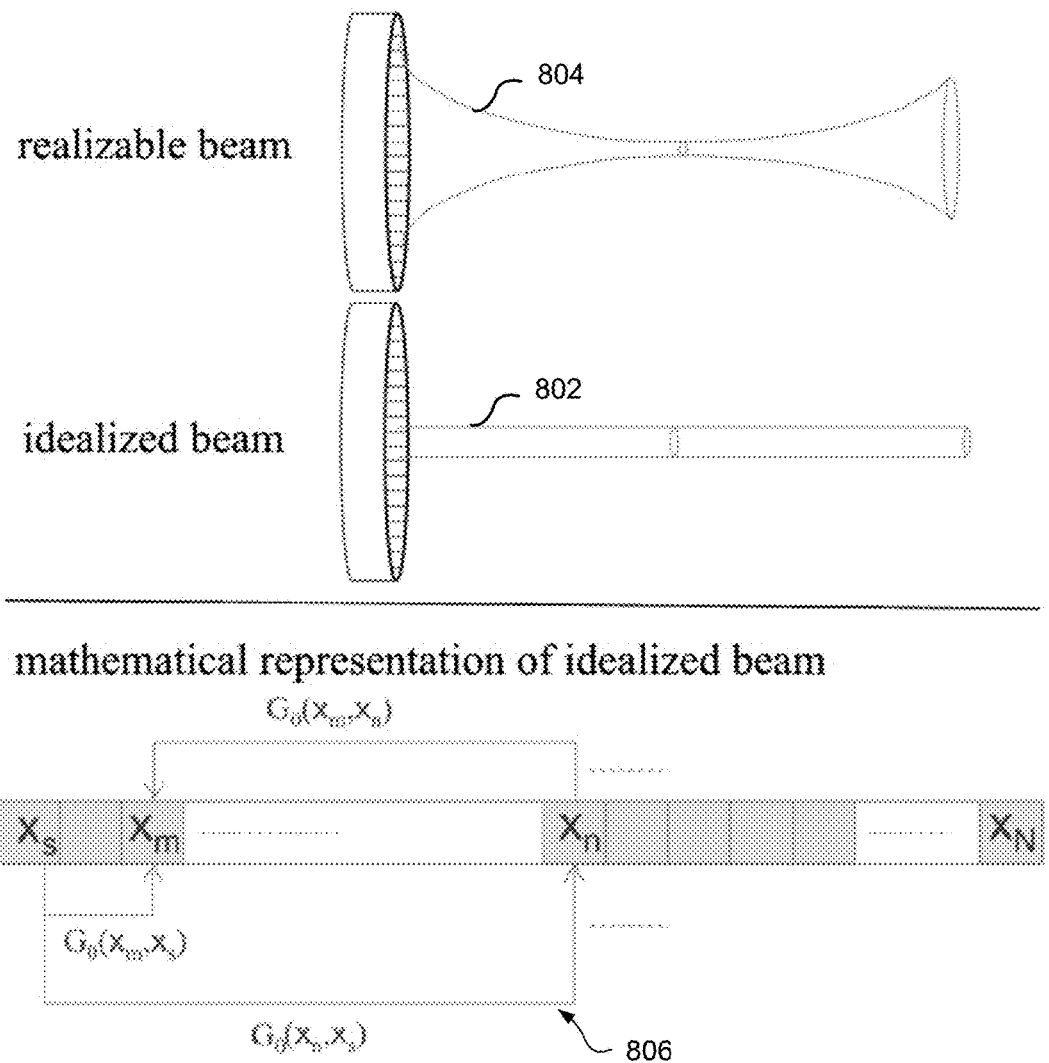
FIG. 8 depicts a one dimensional beam representation.

The domain $\Omega_Z$ contains a one dimensional array of values for the medium. $G_Z$ is the Green's function valid for that domain. $\Omega_n$ becomes the domain covered by the pixel n over which the received energy is reflected back. FIG. 8 depicts an idealized beam 802 and a realizable beam 804 in the one dimensional domain and identifies the homogeneous Green's function components 806 that constitute equation (14).

The discrete version of V(x) is expanded for variable densities and wave velocities encountered at the interface of the scatterer and accommodates entry into a larger scatterer that covers more than one pixel:

$$V(x) = \omega^2 \left[\frac{1}{\rho(x)c^2(x)} - \frac{1}{\rho(x_{n-1})c^2(x_{n-1})}\right] + \nabla \cdot \left[\frac{1}{\rho(x)} - \frac{1}{\rho(x_{n-1})}\right] \nabla. \tag{15}$$

Non-homogeneous wave velocity and density values are identified spatially as c(x) and $\rho$(x) and their counterparts $c(x_{n-1})$ and $\rho(x_{n-1})$ represent the homogeneous values. The reader should note that the terms $$\frac{1}{\rho_0 c_0^2} \text{ and } \frac{1}{\rho_0}$$

have been purposely replaced by $$\frac{1}{\rho(x_{n-1})c^2(x_{n-1})} \text{ and } \frac{1}{\rho(x_{n-1})}$$

respectively. This prevents large discontinuities that occupy multiple continuous pixels from causing extra reflections when there is no wave impedance change encountered between consecutive pixels.

The left hand side of the equation, when implemented in a system, will have $G_Z$ provided by cross correlating received data with the appropriate signature sequence used for transmission. cross-correlation of the additive white Gaussian noise (AWGN) derived sequence and the recovered system response provides an immediate partial solution to the forward problem, that is a portion of the heterogeneous Green's function G, and therefore a more immediate way to find V(x) simplifying the process because the heterogeneous Green's function equivalent is obtained by cross-correlation.

The cross-correlation of the demodulated receive signal with the transmitted AWGN sequence is given by:

$$\hat{g}_k(\tau) = \frac{1}{N\sigma_\kappa \sigma_r} \sum_{n=1}^{N} \kappa(n) r(\tau + n) \quad (16)$$

Where κ represents the AWGN sequence values, r is the demodulated, multi-user decorrelated received signal and $\hat{g}_k$ the estimate for the heterogeneous Greens function for user κ. The result is identical when using a deterministic Kasami sequence instead of a AWGN process. Projecting the heterogeneous correlation response $\hat{g}_k$ on to the one dimensional domain is achieved by applying its result to the expression that represents the heterogeneous wave-field:

$$\hat{g}_k(n) = G_0(x_m, x_s)\delta(n-m) + G_0(x_n, x_s)V(x_n)\int_{\Omega_n} G_0(x_m, x')d\Omega(x'). \quad (17)$$

Four main components construct equation (17). The $G_0(x_n, x_s)\delta(n-m)$ term represents the homogeneous incident wave-field that "short-circuits" straight to the receiver, and the other three terms make up the reflected response that represents the heterogeneity. The term $G_0(x_n, x_s)$ represents the energy that a particular reflection source at location n receives. The amount is scaled by the applicable cross sectional area and is calculated by the f of energy that is reflected versus the amount that penetrates the barrier is represented by V. The amount of reflected energy is scaled by the applicable cross sectional area and is calculated by the $\int_{\Omega_n} G_0(x_m, x')d\Omega(x')$ term. $\hat{g}_k(n)$ represents the correlation power at code offset n. Equation (17) is expanded to its final version for use in variable wave velocity and density scenarios.

$$\hat{g}_k(n) = G_0(x_m, x_s)\delta(n-m) + \omega^2 \left[ \frac{1}{\rho(x)c^2(x)} - \frac{1}{\rho(x_{n-1})c^2(x_{n-1})} \right] \quad (18)$$

$$G_0(x_n, x_s) \int_{\Omega_n} G_0(x_m, x')d\Omega(x') +$$

$$\nabla \cdot \left( \left[ \frac{1}{\rho(x)} - \frac{1}{\rho(x_{n-1})} \right] \nabla \left( G_0(x_n, x_s) \int_{\Omega_n} G_0(x_m, x')d\Omega(x') \right) \right).$$

Equation (18) is the underlying system equation for an acoustic example. It relates the power observed in a bin recovered from the cross-correlation to wave velocity changes and density changes encountered in an otherwise homogeneous medium. Equation (18) assumes a linear domain and that the problem is constrained to a normal angle of incidence.

The Complex Valued Beam Component $\hat{g}_k$

Both amplitude and phase information are represented by Equation (18) in the form of real and imaginary components, in other words two orthogonal components of the wave. Solving the homogeneous wave problem in two dimensions gives:

$$G_0(x_n, x_s) = -\frac{j}{4} H_0^1(v_0|x_s - x_m|).$$

The result provides the amplitude and phase effects implicitly within the real and imaginary components. When recovering the scattered signal that was originally modulated before transmission, the recovered version of the imposed signal is demodulated into both in-phase and quadrature phase components. Cross-correlation with the signature sequence independently against both components gives the amplitudes of the real and imaginary components with respect to the phase of the transmit modulation phase offset. From the amplitudes of the two components the magnitude and phase effect for a wave can be predicted. Implementations that treat the components separately require processes like those stemming from (34) to be carried on each phase. This can be demonstrated using the simple case that consists of two point points, a source point and an observation point in a homogeneous medium.

Example One: Transmitter and Receiver in a Homogeneous Medium

Let a two dimensional space be divided into square subsections (a two dimensional grid) of pixels. If the grid is homogeneous then $V(x_n)$ is zero for all n. Therefore equation (18) reduces to the form $\hat{g}(m) = G_0(x_n, x_s)\delta(n-m)$ and this is explicitly solved with $$\hat{g}(m) = -\frac{j}{4} H_0^1(v_0|x_s - x_m|)$$

where $v_0 = \omega/c_0$, and therefore the solution depends on the frequency chosen and the wave speed in the medium. The result $\hat{g}(m)$ represents the amplitude and phase shift observed at the measuring location $x_m$ given a source at $x_s$. This result can be used to show that the complex result of combining the cross-correlation result for the received in-phase data and the cross-correlation result for the quadrature data with the signature sequence parallels the real and imaginary components of $$-\frac{j}{4} H_0^1(v_0|x_s - x_m|).$$

Intuitively this is not unexpected as the received data is at an unknown phase so demodulation by in oscillator of one phase will not capture all the available signal energy. The combination of one phase along with the signal energy captured by the phase that is orthogonal to the first captures all of the signal energy despite a phase shift between the transmitter and receiver.

Figure 9:
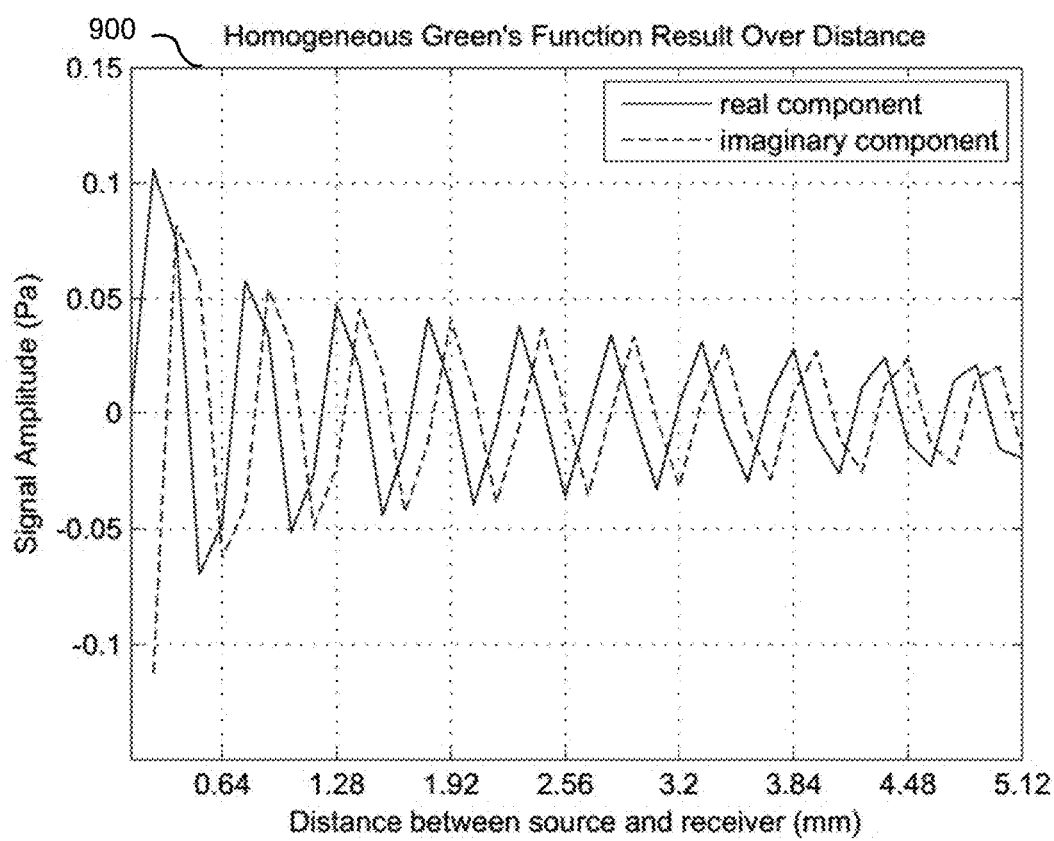
FIG. 9 depicts a homogeneous Green's function result over distance.
Figure 10:
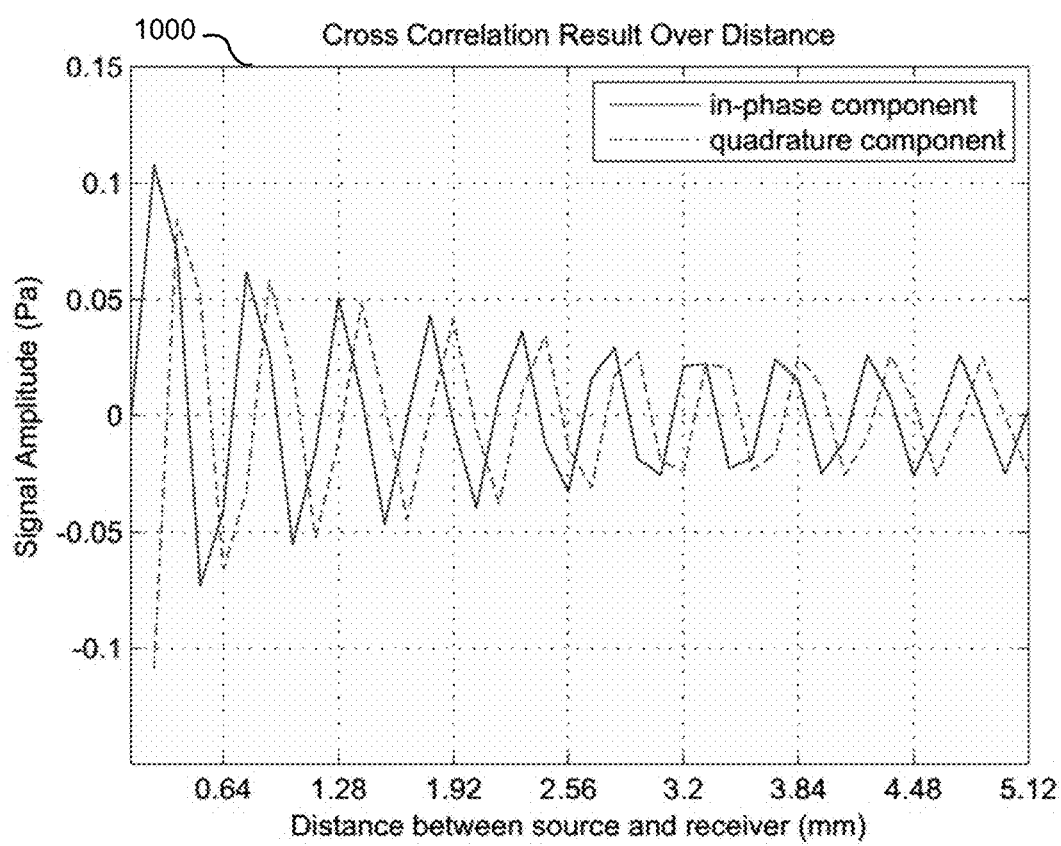
FIG. 10 depicts cross-correlation result over distance.

To demonstrate the complex nature of the Green's Function result with the in-phase and quadrature result of $\hat{g}_k$, the graph 900 in FIG. 9 shows the result of $$-\frac{j}{4} H_0^1(v_0|x_s - x_m|)$$

for a range of distances between the source and receiver while the result taken from a modulated, transmitted, and demodulated deterministic sequence cross correlated with the source signal follows in graph 1000 of FIG. 10.

Normally data for cross-correlation would be provided by recording equipment placed in the environment. For this example a brief simulation provided the data for the cross-correlation of a deterministically generated signal. The homogeneous medium wave velocity was set to 1500 m/s, and the carrier frequency was set to 3 MHz providing enough information to define $v_0$. The signature sequence was taken from the $8^{th}$ degree Kasami Sequence. The Kasami sequence provides an information rich signal that is modulated onto the in-phase carrier and transmitted. For the above demonstration there are no scatterers present, instead the incident signal gain over distance is plotted. For FIG. 10 the result of in-phase and quadrature cross-correlation is recorded and plotted at intervals of 0.0128 m (a value that evenly divides the number of pixels occupying the grid). Demodulation is performed with two orthogonal carrier phases to capture in-phase and quadrature versions of the transmitted signal. Cross-correlation (equation 16) is carried out on both in-phase and quadrature versions to provide the two orthogonal versions of $\hat{g}$. The result provides some confirmation that the homogeneous Green's Function for two points (a source and a measurement location) is equivalent to the result of cross-correlation of the deterministically generated signal measured between the source and measurement locations for the in-phase and quadrature phase offsets.

Expanding on the previous example a discontinuity is defined in the otherwise homogeneous two dimensional grid. The scatterer is given a wave velocity and density unique from the homogeneous medium. In this scenario equation (18) retains its full form. The result $\hat{g}_k(n)$ is the power of a unique code offset and is due only to discontinuities at a fixed distance from the observation point in a mostly homogeneous medium. Reflections from a different distance will not correlate with the code offset specific to the distance affiliated with code offset n and are therefore do not appear in the cross-correlation result. By knowing the speed of the sequence through the medium, a particular sequence offset can be related to a fixed distance (given a homogeneous medium).

Figure 11:
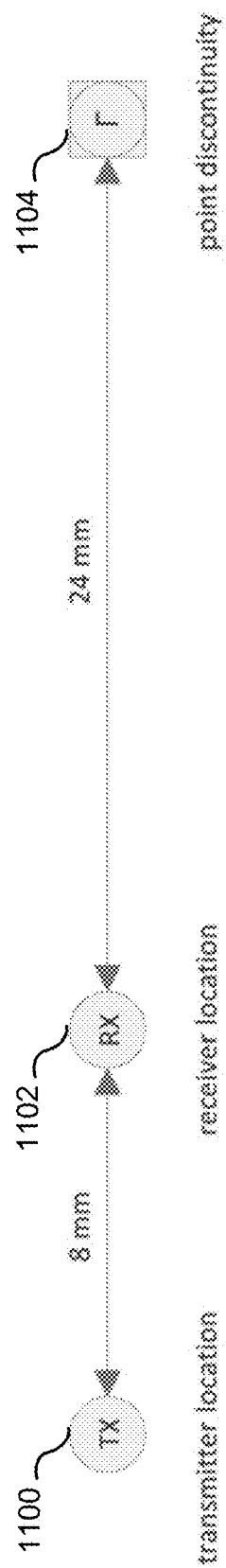
FIG. 11 depicts a layout associated with example two.

For this example let the transmit source 1100 be positioned at x=0 mm, a receiving point 1102 at x=8 mm, and a point discontinuity 1104 at x=32 mm as depicted in FIG. 11.

The medium is excited with a conventional wavelet pulse to show the medium response against the predicted result from equation (18). The pulse is generated with an amplitude of unity, and the sensor values are plotted over time so that the scattered amplitude could be observed. The second brief simulation result is depicted beside the calculated gain and orthogonal component composition in FIG. 12. In the figure, the upper right graph 1202 plots the raw received values at the sensor location. The incident pulse is recorded as well as the scattered version several samples later. In the lower right corner of the figure is a zoomed in graph 1204 of the scattered pulse that is seen and is the result of the imposed pulse being scattered and returning to the sensor. Occupying the left half of the figure, graph 1200 is the calculated magnitude and component responses given the properties of the medium, properties of the scatterer, size of the scatterer, center frequency and the location of the sensor. All these parameters are inputs into equation (18) and the equation provides a prediction of the components of $\hat{g}_k$.

Figure 12:
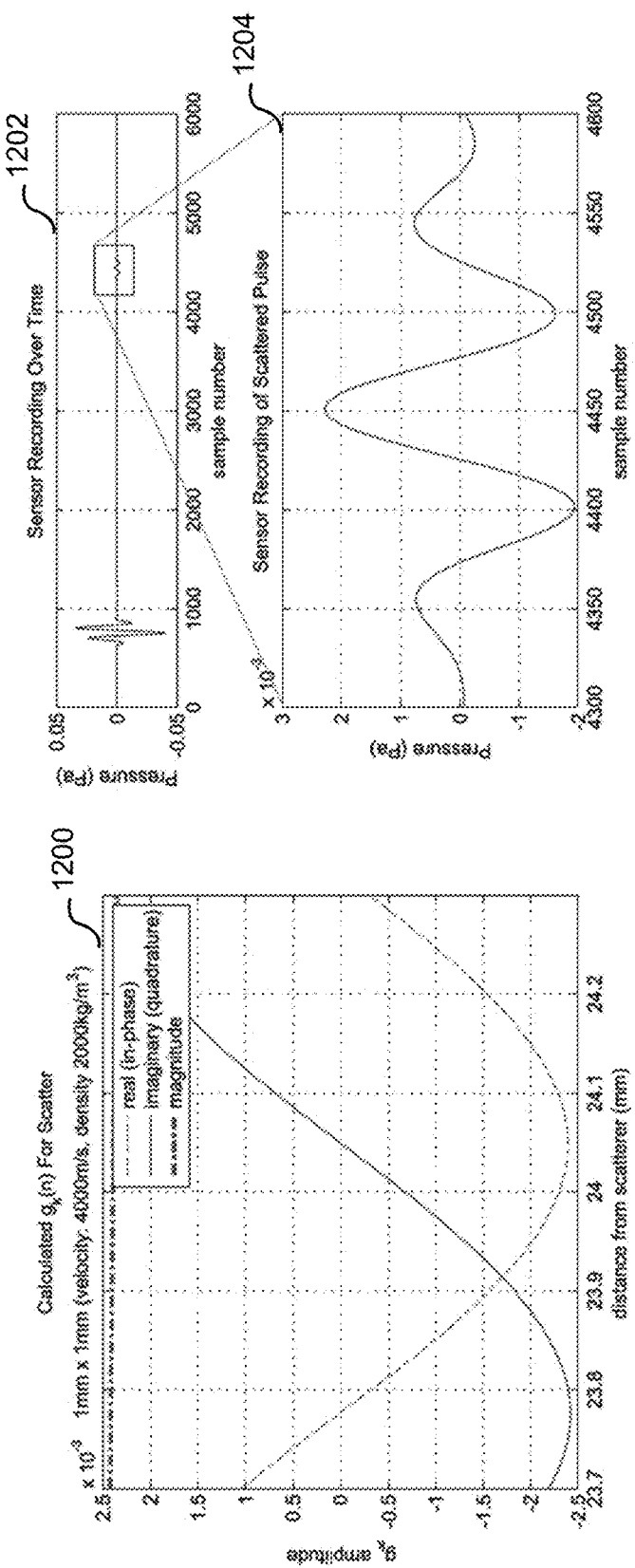
FIG. 12 depicts a conventional example with predicted in-phase and quadrature phase components for a 4000 m/s, 2000 kg/m3 scatterer.

Calculating the gain from the source to the discontinuity and back to the receiver is the role of equation (18) and the result is plotted in the left plot in FIG. 12. The gain seen in the lower right plot corresponds to the predictions shown in the left plot, including the phase reversal observed.

Figure 13:
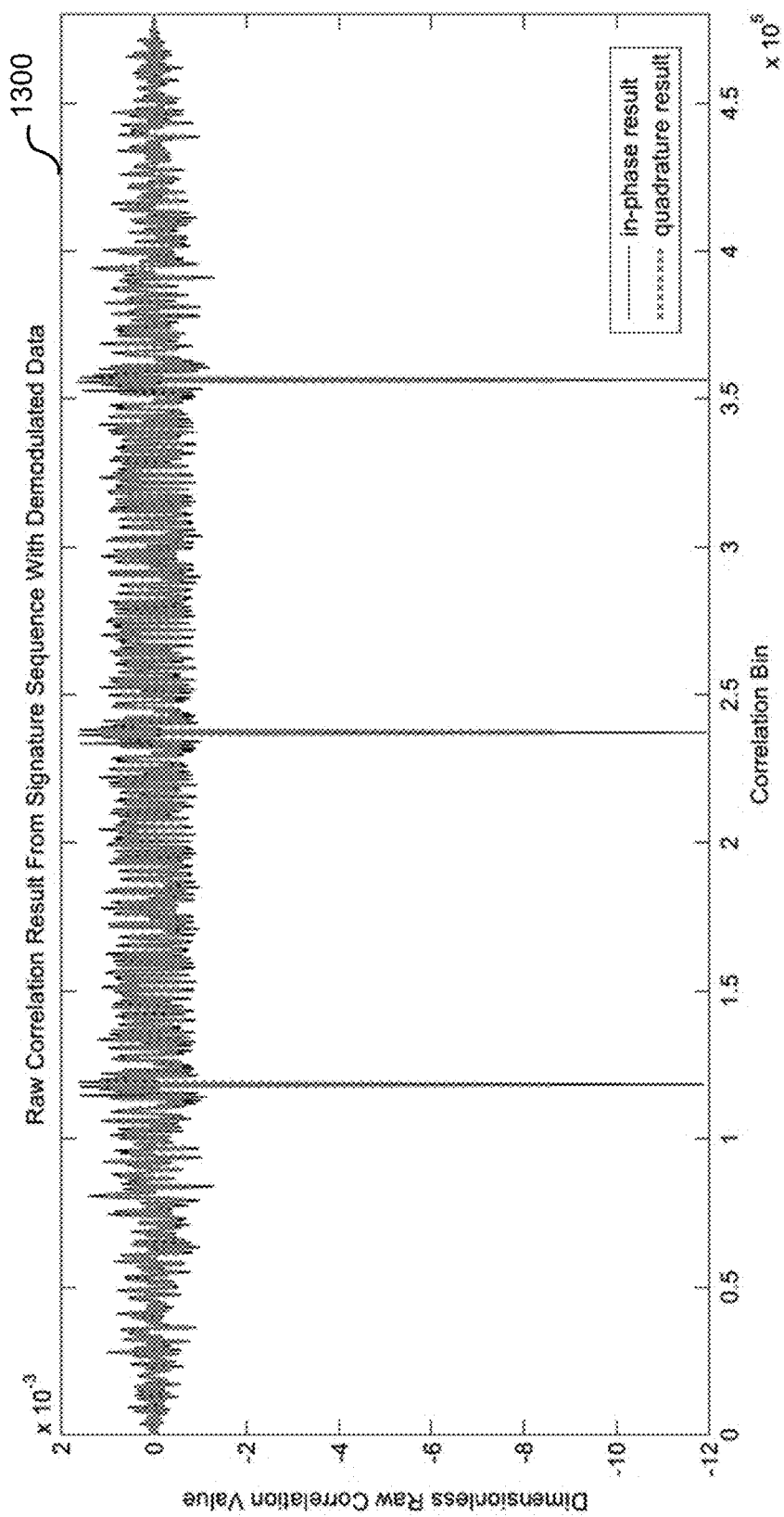
FIG. 13 depicts raw cross-correlation results for signature sequence with demodulated data.

The cross-correlation result of both the in-phase data and the quadrature data from the same media is depicted in graph 1300 of FIG. 13. The in-phase data is captured by the carrier phase synchronized with the transmitter, and therefore the quadrature data is gathered by taking the same received samples and applying demodulation with a carrier phase $$\frac{\pi}{2}$$

radians away from the in-phase carrier. The accumulated demodulated samples are cross correlated with the signature sequence that was used in transmission. The largest component in the result is the line of sight version that arrived first directly from the transmitter. This peak is used to synchronize code offsets to distances away from the receiver.

The code repeated three times in the transmission and therefore three large peaks are present and represent the line of sight version that traveled directly from the transmitter to the receiver. At this stage the components due to scattering are not visible. Since the signature sequence is fully known, the line of sight version can be fully eliminated from the result leaving only the components due to scattering at other code offsets. The decorrelated result is trimmed and realigned to distances relative to the receiver and the results displayed in graph 1400 of FIG. 14. At 24 mm from the receiver, the correlation power due to the scatterer is clearly visible.

Figure 14:
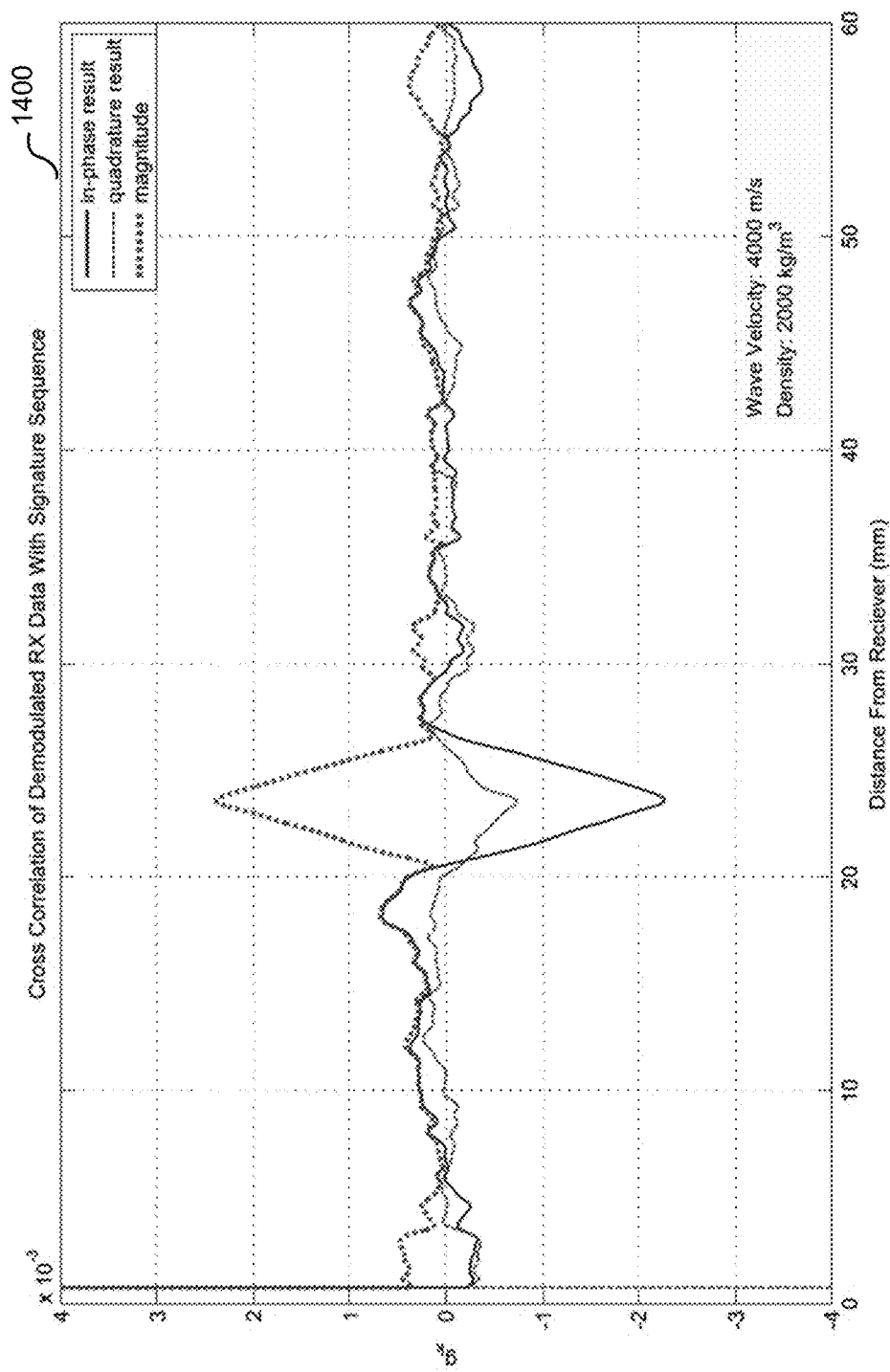
FIG. 14 depicts cross-correlation results for a 4000 m/s, 2000 kg/$m^3$ discontinuity.
Figure 15:
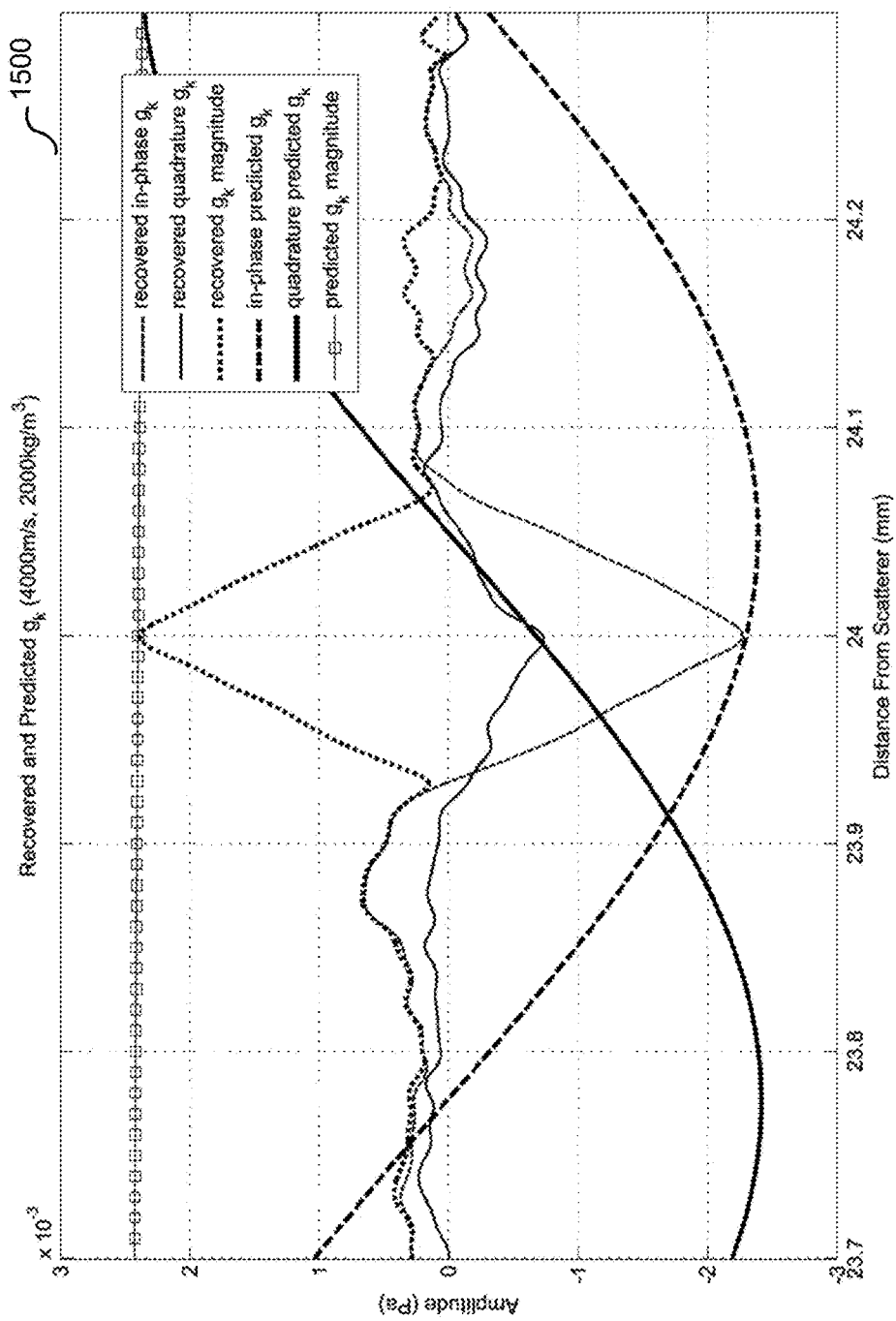
FIG. 15 depicts an overlay of cross-correlation result with predicted in-phase and quadrature phase components for a 4000 m/s, 2000 kg/$m^3$ discontinuity.
Figure 16:
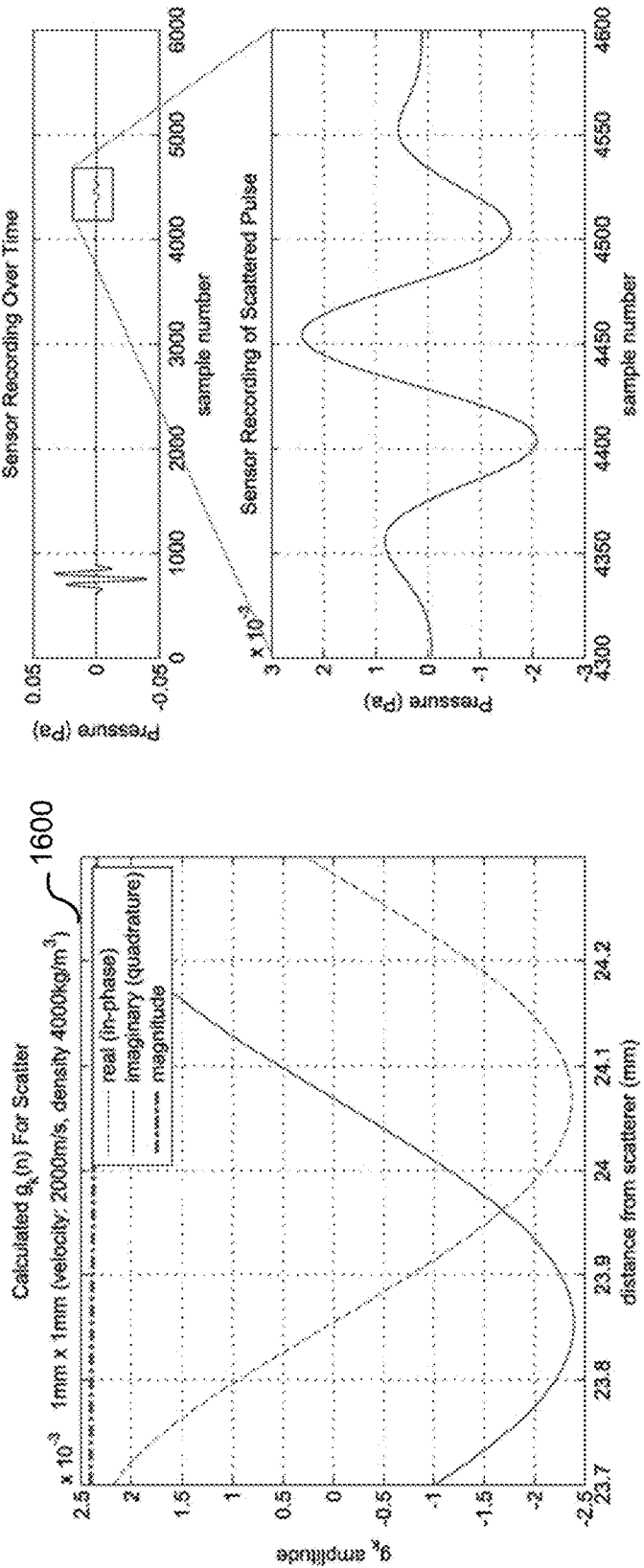
FIG. 16 depicts a conventional example with predicted in-phase and quadrature phase components for a 2000 m/s, 4000 kg/$m^3$ scatterer.
Figure 17:
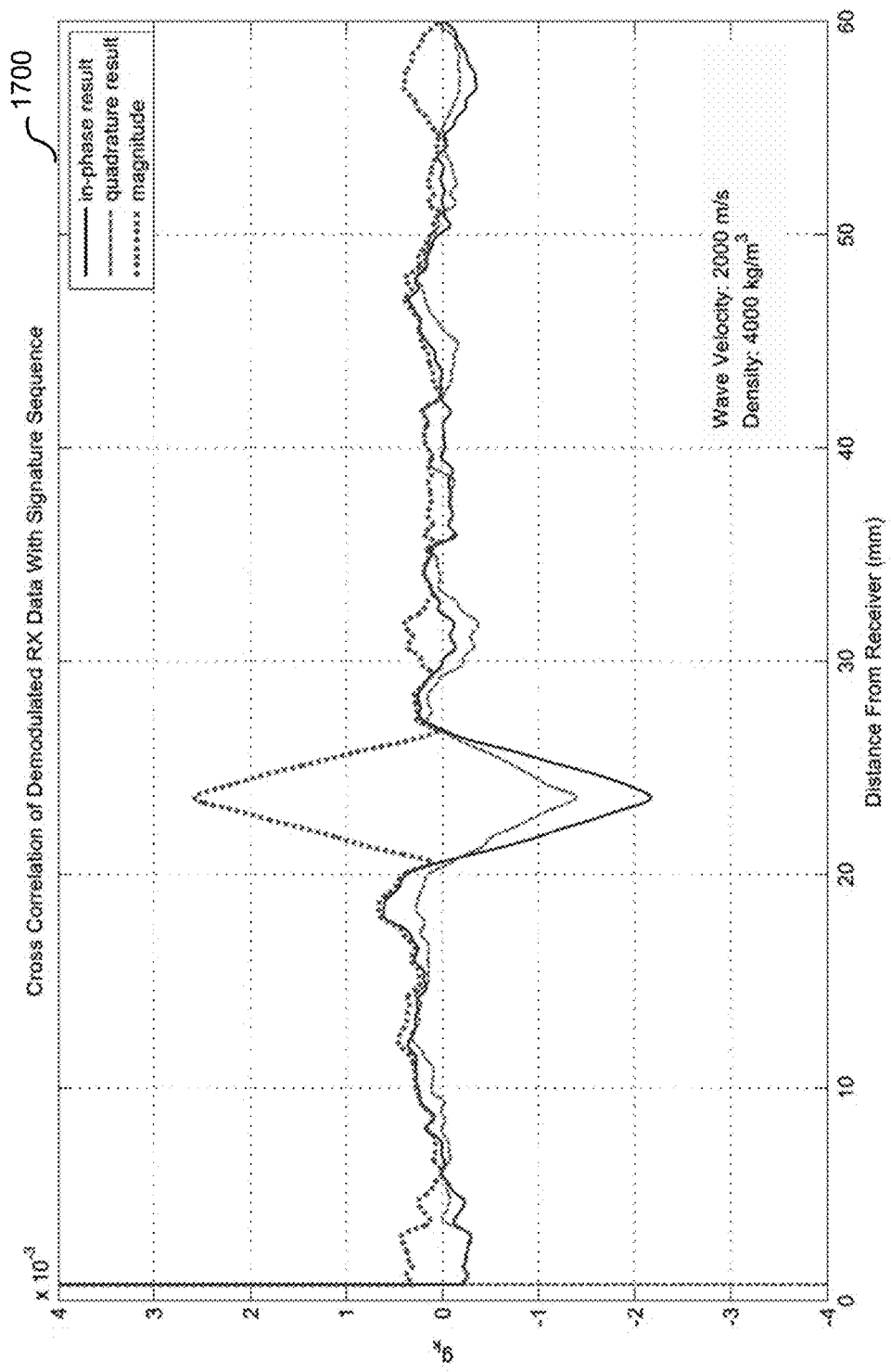
FIG. 17 depicts cross-correlation results for a 2000 m/s, 4000 kg/$m^3$ discontinuity.
Figure 18:
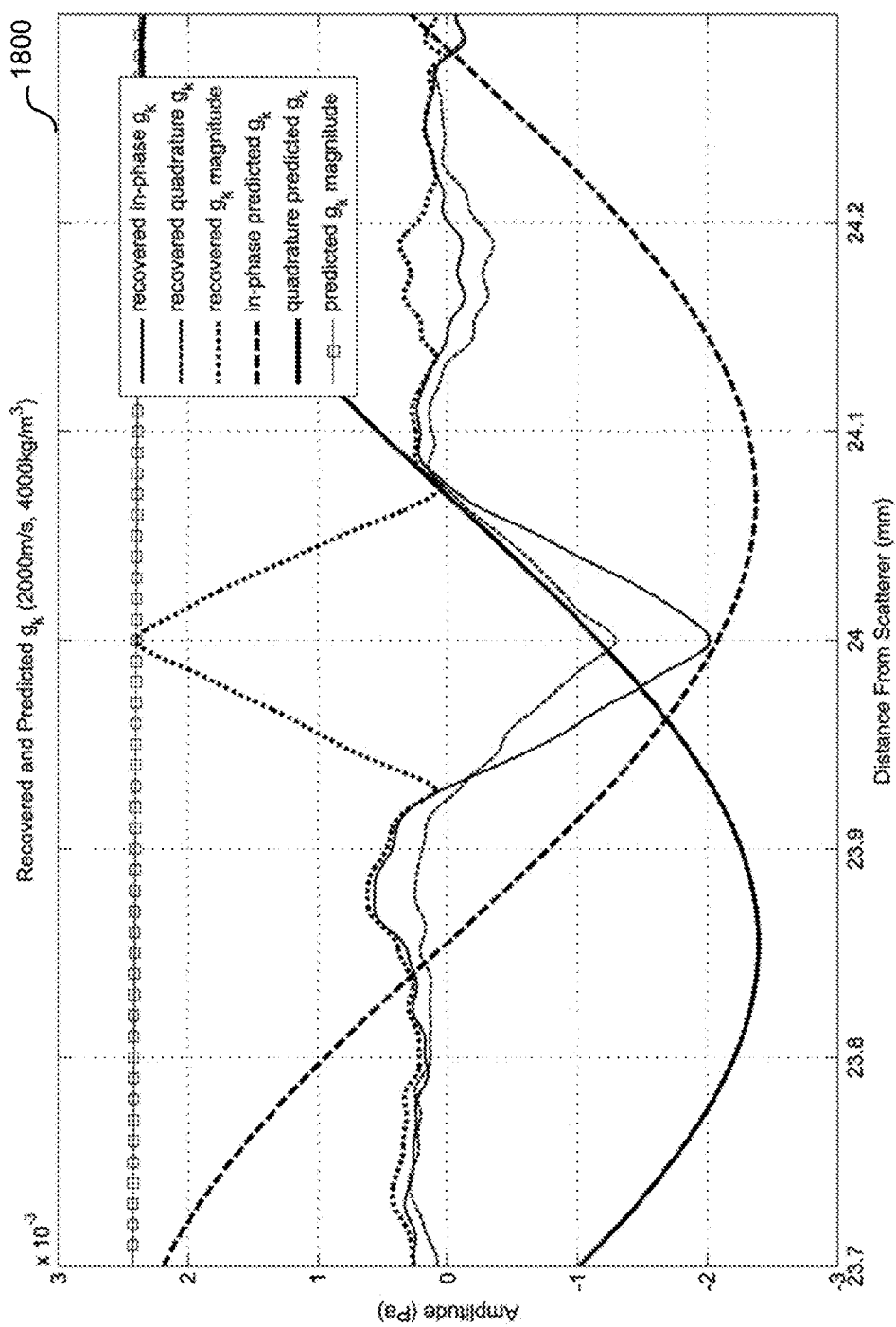
FIG. 18 depicts an overlay of cross-correlation result with predicted in-phase and quadrature phase components for a 2000 m/s, 4000 kg/$m^3$ discontinuity.
Figure 19:
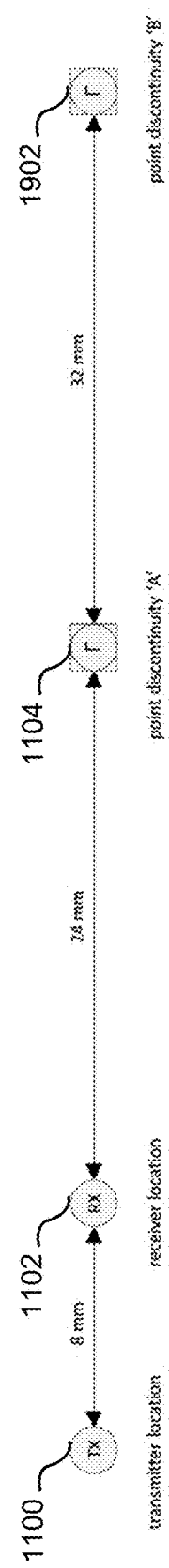
FIG. 19 depicts a layout of example three.
Figure 20:
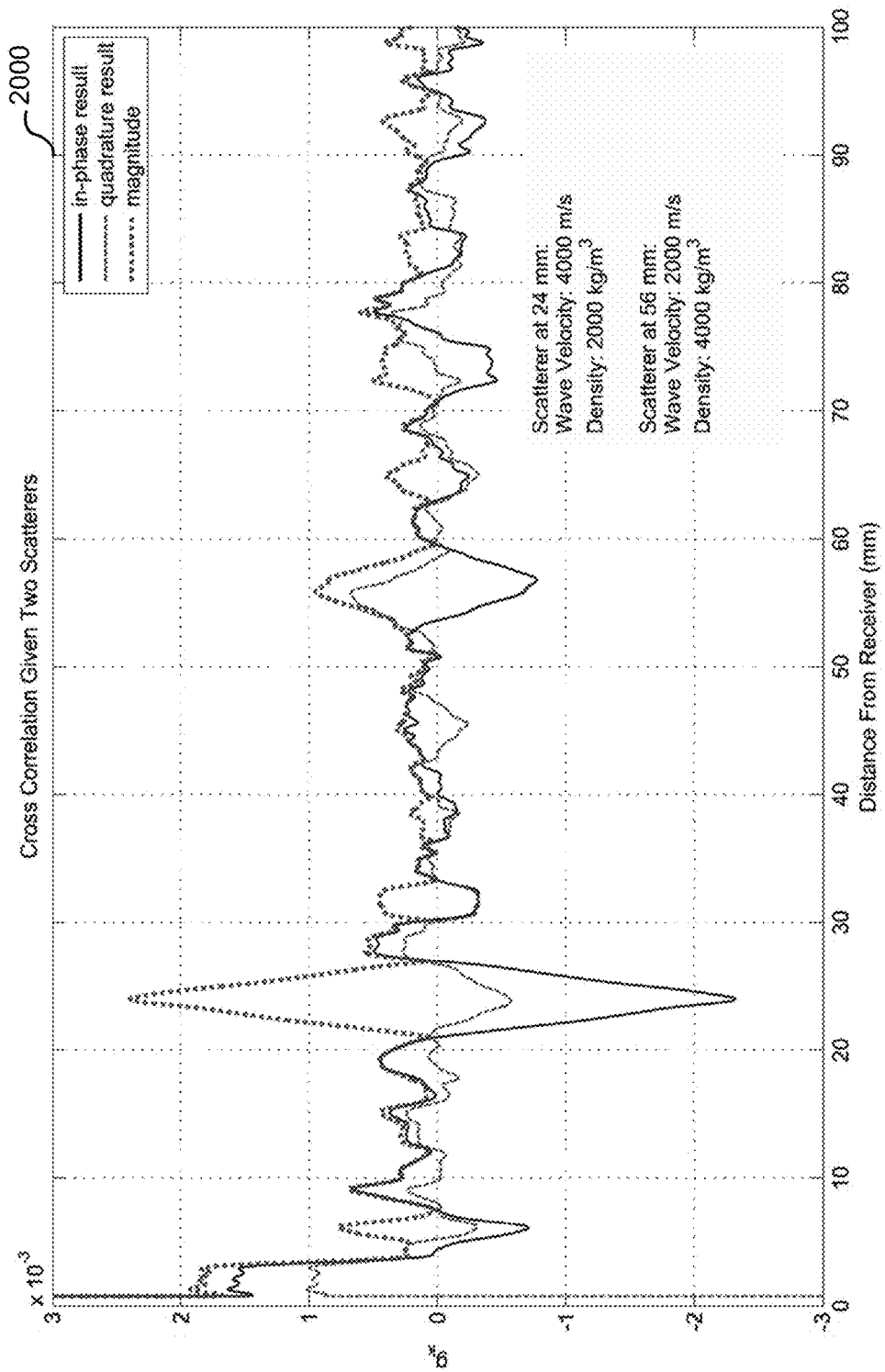
FIG. 20 depicts cross-correlation results with two scatterers.

The result in FIG. 14 is compared against the predicted phase relationship predicted by equation (18). The result of the cross-correlation is overlayed the predicted result in the graph 1500 of FIG. 15. In the figure the expected phase relationships are plotted around the receiver location that is located 24 mm from the scatterer. The recovered phase relationships are effectively the same as the predicted values at a distance of 24 mm from the scatterer. The peaks of the cross-correlation would ideally intersect with the overlayed predictions at the 24 mm location.

To show both the uniqueness and the predictability of the phase relationship given the parameters of the scatterer, the process is repeated but the properties of the scatterer are altered. Data is collected from the third party simulator for the same setup except the scatter's wave velocity and density values are reversed such that where the previous example had a scatterer with an wave velocity of 4000 m/s and a density of 2000 kg/m$^3$, now the scatter has an wave velocity of 2000 m/s and a density of 4000 kg/m$^3$. The impedances are the same so the same magnitude is expected, however, as seen in the scattering equations and equation (18), each property (velocity and density) has a unique relationship with the result. First the environment is excited in a conventional manner with the wavelet pulse and the result is depicted in the graph 1600 FIG. 16 where the predicted magnitude and phase relationships are also displayed.

Receiver data is then collected for the continuous sequence case, demodulated for each phase component and cross correlated with the signature sequence. The short circuit peak is located and its contribution is removed and the result is shown in graph 1700 of FIG. 17.

Although the magnitude of the reflection is the same, the relative contribution of each component is different than that seen in FIG. 14 where the acoustic properties were different. In the case of the previous scatterer, the peaks of the components were more varied in their respective contributions. In this case the phase amplitude contributions have become closer. The correlation result is overlayed on top of the prediction in graph 1800 of FIG. 18.

Again there is agreement between the predicted and recovered phase relationships at the 24 mm location. When reviewing FIGS. 12, 16, 15 and 18 it is observed that the phase shift of the in-phase and quadrature phase components changes as the components that define the scatterer change. The amount of energy reflected is proportional to the acoustic impedance change encountered and may result in identical acoustic impedances even though the scatterer properties are unique. By definition acoustic impedance $z=\rho c$, therefore there are several values for $\rho$ and c that correspond to the same impedance value. Fortunately different arrangements of $\rho$ and c that may have the same impedance have unique relationships between their in-phase and quadrature phase components as is seen by inspecting FIGS. 12 and 16. The phase relationship (in terms of amplitude) follows what is predicted when compared to the relative signal power found in the orthogonal demodulated phases. Although it would seem there are two unknowns and only one equation, because the equation is complex there are effectively two orthogonal equations that constitute the overall equation providing two equations for two unknowns.

Example Three: Two Discontinuities

Expanding upon the previous example, another discontinuity is added to the medium. The new scatterer 1902 is placed 32 mm further away from the first scatterer. The layout is portrayed in FIG. 19.

The first scatterer is given an acoustic impedance of 8 MPa·s/m$^3$ (wave velocity 4000 m/s, density 2000 kg/m$^3$). The second scatterer is given the same acoustic impedance however the values for wave velocity and density are swapped to 2000 m/s and 4000 kg/m$^3$ respectively. The scattering result for the first discontinuity in the medium is already predicted above, shown in FIG. 15. The predicted gain component values for a discontinuity 56 mm away with a wave velocity of 2000 m/s and density of 4000 kg/m$^3$ are $(-8.883+j\ 7.621)\times 10^{-4}$. The same Kasami sequence is employed that was used previously. The cross-correlation result after transmission and recovery is shown in graph 2000 in FIG. 20.

The first observable pulse at 24 mm is effectively identical to the single scatterer case. The impact of the second scatterer can be observed at the 56 mm mark. To verify identification based on the in-phase and quadrature phase components the portion of the correlation response in the vicinity of the 56 mm mark is overlayed onto the prediction calculated by equation (18) in graph 2100 of FIG. 21.

Figure 21:
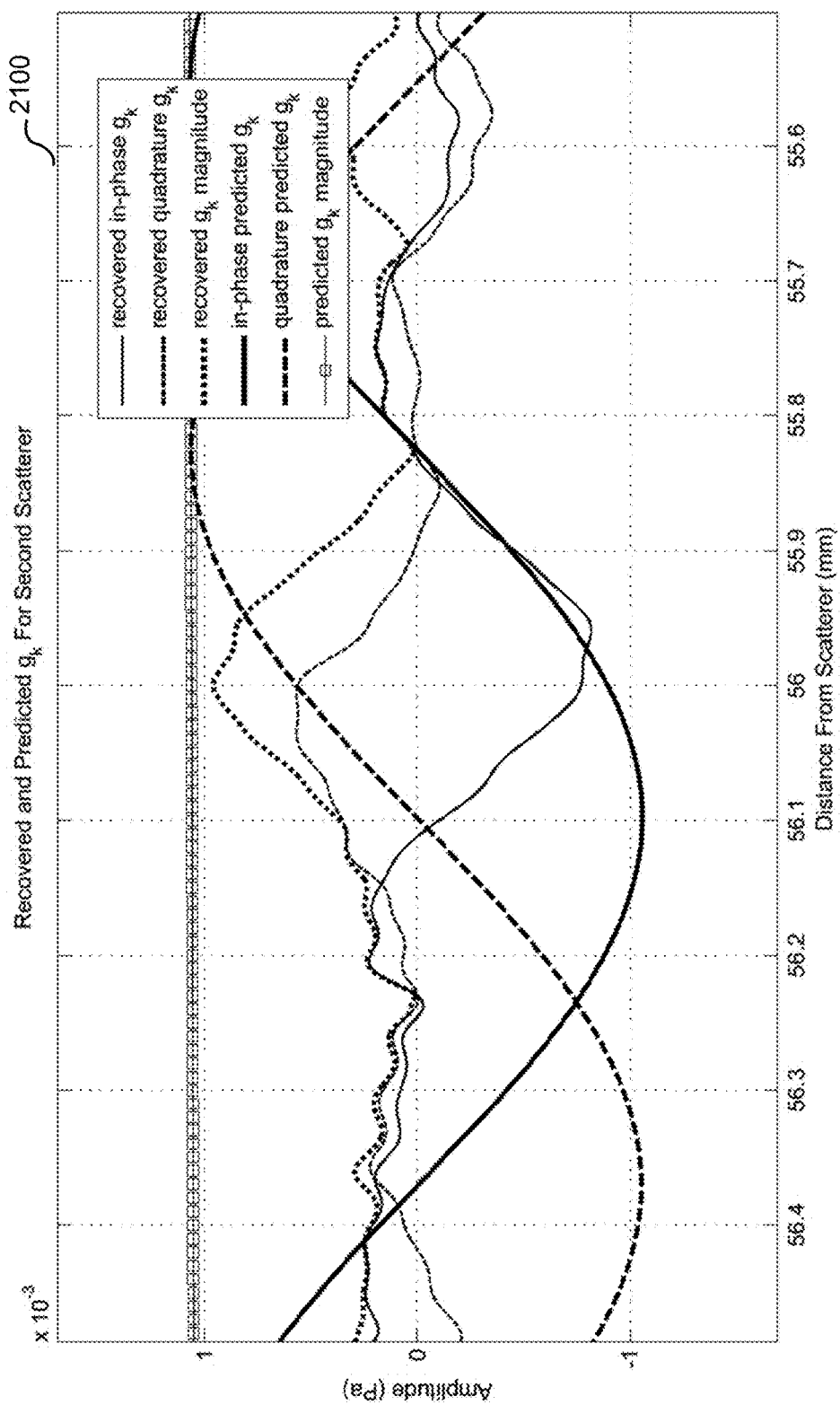
FIG. 21 depicts a cross-correlation overlayed on predicted component values.

As seen in graph 2100 of FIG. 21 the recovered gain components are $(-8.033+j\ 7.980)\times 10^{-4}$. Recall, according to equation (18), the predicted components were $(-8.883+j\ 7.621)\times 10^{-4}$. Had the scatterer parameters been identical to the first (wave velocity of 4000 m/s and 2000 kg/m$^3$) the predicted phase component peaks would have been $(-3.692+j\ 10.55)\times 10^{-4}$. Although the acoustic impedance is the same, the component values are significantly different allowing for the wave velocity and density to be uniquely identifiable.

Signal Decorrelation for Green Function Retrieval

The near orthogonal deterministic sequences with favorable cross-correlation properties enable the superposition and later separation of multiple transmitters/receivers (users) in the system running concurrently in the same frequency range that is optimal for the medium and equipment. In a potential group of foreign signals from different users it is desired to recover a specific user's own influence on the medium among the collective. The assumption made that enables the ability to isolate the specific user's contribution is that the signature sequences of the other users in the system are known.

The composite signal detected by the receiver can be expressed as $$r(t)=s(t)+n(t) \tag{19}$$

where r(t) is the received signal, s(t) is the composite transmitted signal convolved with the environment and n(t) represents the composite noise signal. s is a sum of individual components sourced from K transmitters and is defined as $$s(t)=\Sigma_{k=1}^{K} s_k(t-\tau_k). \tag{20}$$

Each $s_k(t)$ is composed of the product of a specific signature waveform $k_t$ and the channel response or Green's function component g(i) expressed as $$s_k(t)=\sqrt{\epsilon_k}\Sigma_{i=1}^{N} g_k(i)\kappa_k(t-iT) \tag{21}$$

where $\epsilon$ represents the energy per bit. The signature waveform $k_k$ is constructed from a deterministically generated pulse sequence function consisting of values±1, each lasting for a single bit period T and having an impulse autocorrelation property. The transmitted sequence is altered by being convolved by the effects of the medium represented by $g_k$.

The expanded version of the signals as they exist in the medium can be expressed as:

$$s(t)=\Sigma_{k=1}^{K}\sqrt{\epsilon_k}\Sigma_{i=1}^{N} g_k(i)\kappa_k(t-iT-\tau_k). \tag{22}$$

It should be noted that not only is the user's signature sequence treated as unique, but the medium's response to that particular user is treated as unique also. The individual $g_k$ holds the system response to the particular user k. In order to determine if the information of user k is contained in s the probability that s contains $k_k$ is evaluated. This process begins by constructing a parameter vector $\theta$ consisting of the parameters $[k_k\ g_k]$ so that s is defined by the parameter vector $\theta$ and therefore s is expressed as s(t; $\theta$). The maximum a posteriori probability criteria that maximizes the probability that r is received given an estimate of $\theta$ from which the transmitted signal is derived is given as:

$$p(\theta|r)=\frac{p(r|\theta)p(\theta)}{p(r)} \tag{23}$$

which implies if $\rho(\theta)$ is constant then the $\theta$ that maximizes r, maximizes $\rho(r|\theta)$ and since they are proportionally related $\rho(\theta|r)$ is maximized also.

The joint PDF $\rho(r|\theta)$ for the additive white zero mean Gaussian signals in the environment including n(t) is expressed as $$p(r|\theta)=\left(\frac{1}{\sqrt{2\pi}\ \sigma}\right)^N \exp\left\{-\sum_{n=1}^{N}\frac{[r_n-s_n(\theta)]^2}{2\sigma^2}\right\} \tag{24}$$

Where $r_n=\int_{T_0} r(t)\phi_n(t)dt$ are orthonormal functions used to expand r(t) and s(t; $\theta$) into vector coefficients.

The maximization of (24) is equivalent to maximization of the likelihood function:

$$\Lambda(\theta) = \exp\left\{-\frac{1}{N_0}\int_0^{NT+2T}[r(t)-s(t;\theta)]^2 dt\right\} \quad (25)$$

considering that in an asynchronous system there will be two consecutive symbols from all other users that overlap with a desired symbol. The exponential function is monotonic and therefore the resulting likelihood is not affected when removed by taking the logarithm of both sides. Constant terms do not add relevant information from a perspective of likelihood thus the term $$-\frac{1}{N_0}$$

is removed giving:

$$\hat{\Lambda}(\theta) = \int_0^{NT+2T}[r(t)-s(t;\theta)]^2 dt. \quad (26)$$

Substitution of the multi-user transmitted waveform leads to the likelihood function:

$$\hat{\Lambda}(g) = \int_0^{NT+2T}[r(t) - \sum_{k=1}^{K}\sqrt{\epsilon_k}\sum_{i=1}^{N}g(i)\kappa_k(t-iT-\tau_k)]^2 dt \quad (27)$$

And reduces to the linear system:

$$\hat{\hat{\Lambda}}(g) = (r - R_N g)^\top R_N^{-1}(r - R_N g) \quad (28)$$

Where $R_N$ is defined as:

$$R_N = \begin{bmatrix} R_K(0) & R_K(1) & 0 & \cdots & \cdots \\ R_K^T(1) & R_K(0) & R_K(1) & 0 & \cdots \\ 0 & \ddots & \ddots & \ddots & \ddots \\ \vdots & \ddots & R_K^T(1) & R_K(0) & R_K(1) \\ 0 & 0 & 0 & R_K^T(1) & R_K(0) \end{bmatrix}. \quad (29)$$

The internal $R_K(m)$ is a K×K matrix where each element is defined as $R_{ij} = \int_{-\infty}^{\infty} k_i(t-\tau_i)k_j(t+mT-\tau_j)dt$. The r matrix is constructed with components:

$$r_k(i) = \int_{iT+\tau_k}^{(i+1)T+\tau_k} r(t)\kappa_k(t-iT-\tau_k)dt, 1 \le i \le N \quad (30)$$

and assembled according to $$r = [r^\top(1) r^\top(2) \ldots r^\top(N)]^\top$$

$$r(i) = [r_1(i)r_2(i) \ldots r_K(i)]^\top \quad (31)$$

and the g matrix is constructed as:

$$g = [g^\top(1)g^\top(2) \ldots g^\top(N)]^\top$$

$$g(i) = [\sqrt{\epsilon_1}g_1(i)\sqrt{\epsilon_2}g_2(i) \ldots \sqrt{\epsilon_K}g_K(i)]^\top \quad (32)$$

and finally $$n = [n^\top(1)n^\top(2) \ldots n^\top(N)]^\top$$

$$n(i) = [n_1(i)n_2(i) \ldots n_K(i)]. \quad (33)$$

Given equation (28), the estimate of all the $\hat{g}$'s for all the users is assembled in g and is the result from:

$$\hat{g} = R_N^{-1} r \quad (34)$$

And given $$r = R_N g + n. \quad (35)$$

$$\hat{g}_k = R_N^{-1} r_k \quad (36)$$

The estimate $\hat{g}$ is the cross-correlation of κ and r with the multi-user interference decorrelated. Construction of the $R_N$ matrix assumed that the multi-user asynchronous delays $\tau_k$ were known. Acquisition of the inter-user time offset is accomplished by cross-correlation of each user's signature code with a frame of the received signal at each particular user's receiver. The time offset of the peaks of the correlation result for each user is noted for $\tau_k$. It is noted that in a typical message transmission implementation $\hat{g}$ would normally hold the unique baseband message to be transmitted and recovered. In this work $\hat{g}$ is defined by the medium and is conveniently equivalent to the system response.

Equation 34 Usage

Equations (18) and (34) are partners in enabling continuous multi-user imaging, and are central equations presented herein. Equation (34) extracts an individual user's cross-correlation result from the ensemble operating in the environment so that equation (18) can map the result into phase amplitudes which can then be mapped to the acoustic velocity and density of the scatterers within the environment. Illustrated here is an example on how the equation is populated and demonstrates the removal of inter-user interference. Before Equation (18) can be employed it is set up indirectly by expanding Equation (35). Consider a two user case; presuming the relative delays, $\tau_k$, are known for a two user system then from (35) the information is assembled as follows:

$$\begin{bmatrix} r_1(1) \\ r_2(1) \\ r_1(2) \\ r_2(2) \\ r_1(3) \\ r_2(3) \\ \vdots \end{bmatrix} = \begin{bmatrix} 1 & r_{12}(0) & r_{11}(1) & r_{12}(1) & 0 & 0 \\ r_{21}(0) & 1 & r_{21}(1) & r_{22}(1) & 0 & 0 & \ddots \\ r_{11}(1) & r_{21}(1) & 1 & r_{12}(0) & r_{11}(1) & r_{12}(1) & \ddots \\ r_{12}(1) & r_{22}(1) & r_{21}(0) & 1 & r_{12}(1) & r_{22}(1) & \ddots \\ 0 & 0 & r_{11}(1) & r_{21}(1) & 1 & r_{12}(0) & \ddots \\ 0 & 0 & r_{12}(1) & r_{22}(1) & r_{21}(0) & 1 & \ddots \\ & \ddots & \ddots & \ddots & \ddots & \ddots & \ddots \end{bmatrix} \begin{bmatrix} g_1(1) \\ g_2(1) \\ g_1(2) \\ g_2(2) \\ g_1(3) \\ g_2(3) \\ \vdots \end{bmatrix} \quad (37)$$

By examining the receive window surrounding a particular symbol of interest it becomes apparent that consecutive symbols from all users around the symbol of interest need to be accommodated. In addition, the symbol of interest for a user of interest also shares the receive window with either an earlier or later symbol in the sequence. If one of the components of the system is expanded, the contribution of all the possibilities of overlap can be verified. Taking $r_1(2)$ as an example:

$$r_1(2) = \int_{2T+\tau_1}^{3T+\tau_1} r(t)\kappa_1(t - 2T - \tau_1)dt \quad (38)$$

$$= r_{11}(1)g_1(1) + r_{21}(1)g_2(1) + g_1(2) + r_{12}(0)g_2(2) +$$

$$r_{11}(1)g_1(3) + r_{12}(1)g_2(3)$$

From the asynchronous system a given component in the received waveform is correlated against a specific signature sequence ($r_1(2)$ for example) and is a combination of overlapping symbols from sequence components of all users. The purpose of this system is not to solve for $r_1(2)$ however. The $r_k(n)$ terms are given, and the cross-correlations that make up $R_N$ are easily calculated. The purpose of this system is to find the $g_k(n)$ terms which requires the inverse of $R_N$.

A scenario that allows for easy inversion of the $R_N$ matrix follows for illustration purposes. Suppose the two user system is synchronous such that there is only one symbol that interferes with the symbol of interest. In this scenario $R_N$ reduces to:

$$R_N = \begin{bmatrix} 1 & r_{12}(0) \\ r_{21}(0) & 1 \end{bmatrix} \tag{39}$$

Therefore $$R_N^{-1} = \frac{1}{1 - r_{12}(0)^2} \begin{bmatrix} 1 & -r_{12}(0) \\ -r_{21}(0) & 1 \end{bmatrix} \tag{40}$$

To isolate a discrete sample of the received waveform r(t) to observe the effect for a symbol of interest let the discrete version of r(t) be represented as $r_i = \int_{T_0} r(t)\phi_i(t)dt$. It then follows:

$$r_i = \int_{T_0} r(t)\phi_i(t)dt = \sqrt{\epsilon_1} g_1(i)\kappa_1(t-iT) + \sqrt{\epsilon_2} g_2(i)\kappa_2(t-iT) + n(t) \tag{41}$$

The result of correlating $r_i$ with the two signature sequences $\kappa_1$ and $\kappa_2$ produces the two user term $r_2(i)$ (recall Equation (30)):

$$r_2(i) = \begin{bmatrix} \sqrt{\epsilon_1}\, g_1(i) + r_{12}(0)\sqrt{\epsilon_2}\, g_2(i) + n_1 \\ r_{12}(0)\sqrt{\epsilon_1}\, g_1(i) + \sqrt{\epsilon_2}\, g_2(i) + n_2 \end{bmatrix} \tag{42}$$

The unwanted inter-user components are clearly seen in $r_2$. It is desirable to isolate $g_1$ from $g_2$. Applying $R_N^{-1}$ to $r_2$ (recall $\hat{g} = R_N^{-1} r$) produces:

$$\hat{g}(i) = \begin{bmatrix} \sqrt{\epsilon_1}\, g_1(i) + (n_1 - r_{12}(0)n_2)/(1 - r_{12}(0)^2) \\ \sqrt{\epsilon_2}\, g_2(i) + (n_2 - r_{12}(0)n_1)/(1 - r_{12}(0)^2) \end{bmatrix} \tag{43}$$

This shows that it is theoretically possible to completely remove the inter-user distortion. The result for $\hat{g}$ for a specific user contains no information from any of the other users. Noise components affiliated with other users is noted in the $$(n_1 - R_{12}(0)/(1 - r_{12}(0)^2)$$

term.

Decorrelation Example

Figure 22:
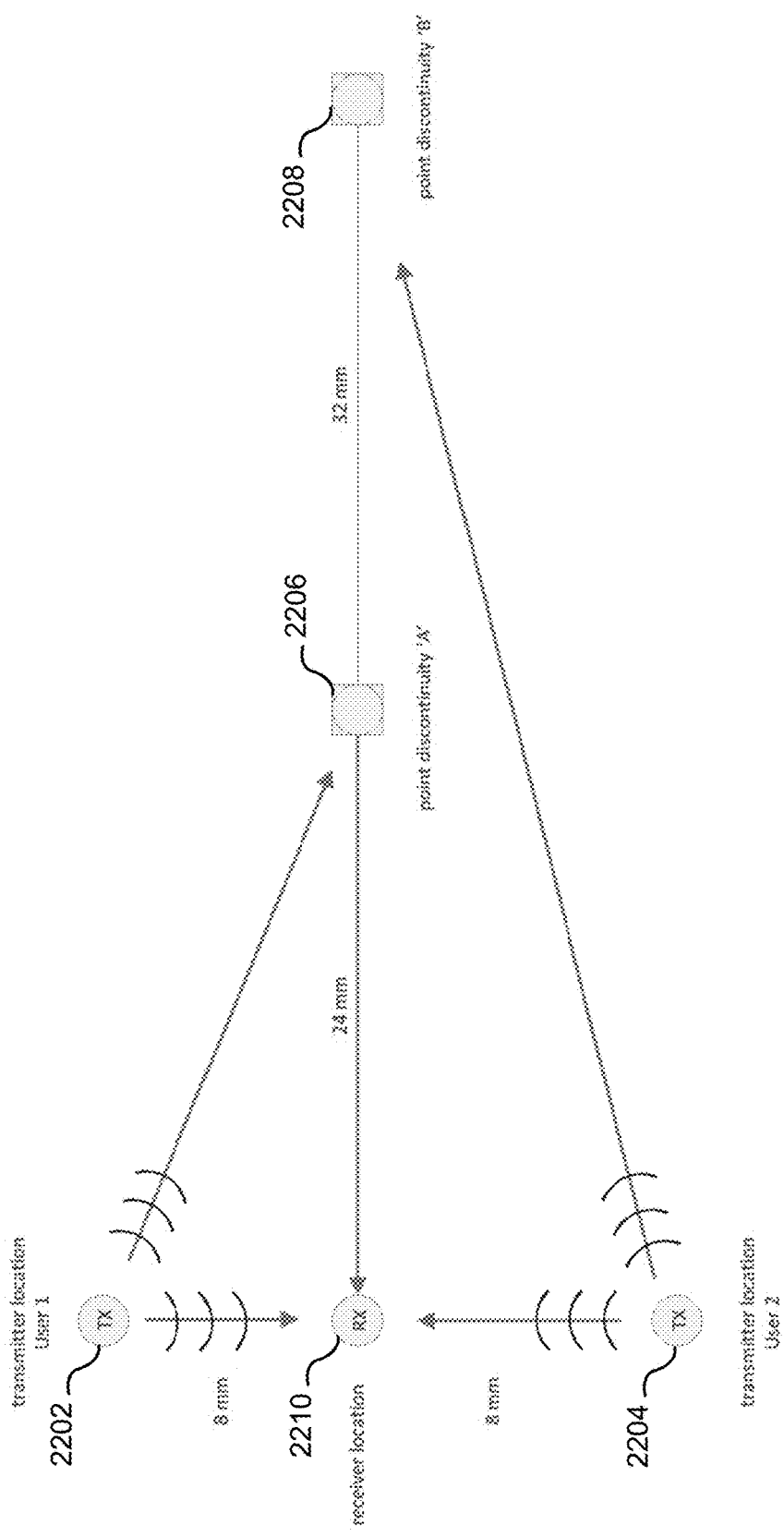
FIG. 22 depicts a multi-user imaging layout.

In application there are a couple different scenarios where multiple imagers would be operating in the same environment. In one scenario multiple imagers are imaging the exact same object or scatterers and therefore their correlation responses might intend to be near identical. In other scenarios the users may be operating in the same medium but focusing on different portions of an object of interest. In this scenario the recovered $\hat{g}$ for each user would be unique even though their incident and scattered waves overlap and arrive at another user's receiver. In this example the second scenario is implemented. FIG. 22 illustrates the concept.

Two users are operating with unique transmitters 2202, 2204 that are focused on specific scatterers 2206, 2208 in the medium but share the same receiver 2210. Therefore even though each user will have the scattered information of the other user's incident waveform, the other user's scatterer should not show up in their own $\hat{g}$. In this scenario both users are transmitting at the same power level, and the transmitted signals are allowed to short circuit to the receiver over the same distance. From one user's perspective there is a noise source in the environment that is broadcasting at the same power level. Each scatterer is 3 mm×3 mm and the first (24 mm away from the receiver) has acoustic properties of 4000 m/s and 5000 kg/m3 while the second is parameterized with 5000 m/s and 4000 kg/m3.

Each user is assigned an 8th order Kasami sequence to use as their signature sequence. Modulation is performed the same way for both users.

Figure 23:
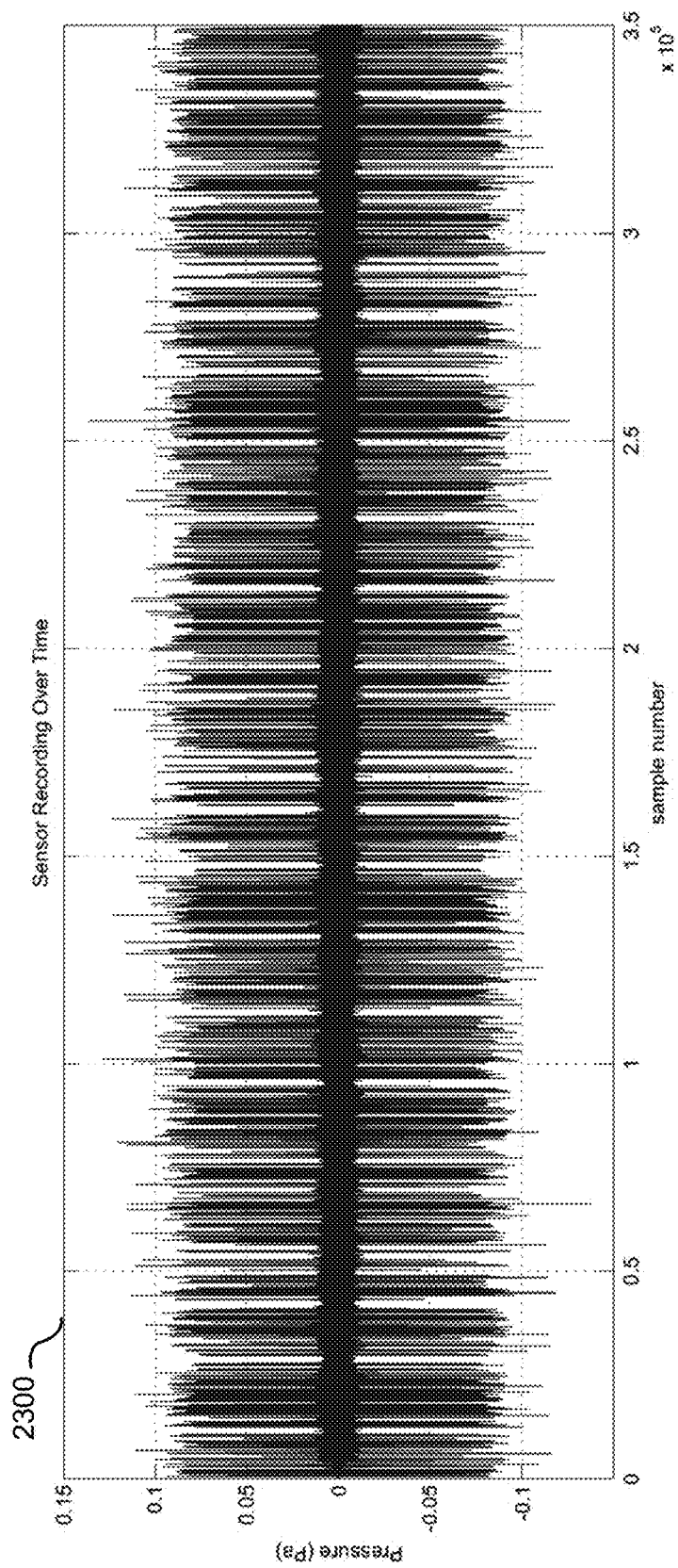
FIG. 23 depicts raw receiver data from two transmissions and scattering.

The graph 2300 in FIG. 23 shows the receiver recording. Significant signal fading (giving the appearance of gaps in the transmission) can be observed due to the multi-user interference where the incident signals meet at the receiver. The following description iterates through the steps required for the foreign user deconvolution, explaining the process of populating equation (34). First demodulation is performed by the user, and then cross-correlation is performed with each user's signature sequence. This is performing the operation described by equation (30) allowing equation (42) to be built. Noting the offsets of each user in the receive data when each user's sequence was cross correlated with the raw receive data provides the inter-user delay. The delays are used to properly align each user's code before cross correlating each user's sequence with all foreign users' signature sequence in order to build the $R_N$ matrix as in equation (29). $R_N$ is then inverted and applied to r to provide the individual unique medium responses for each user.

Figure 24:
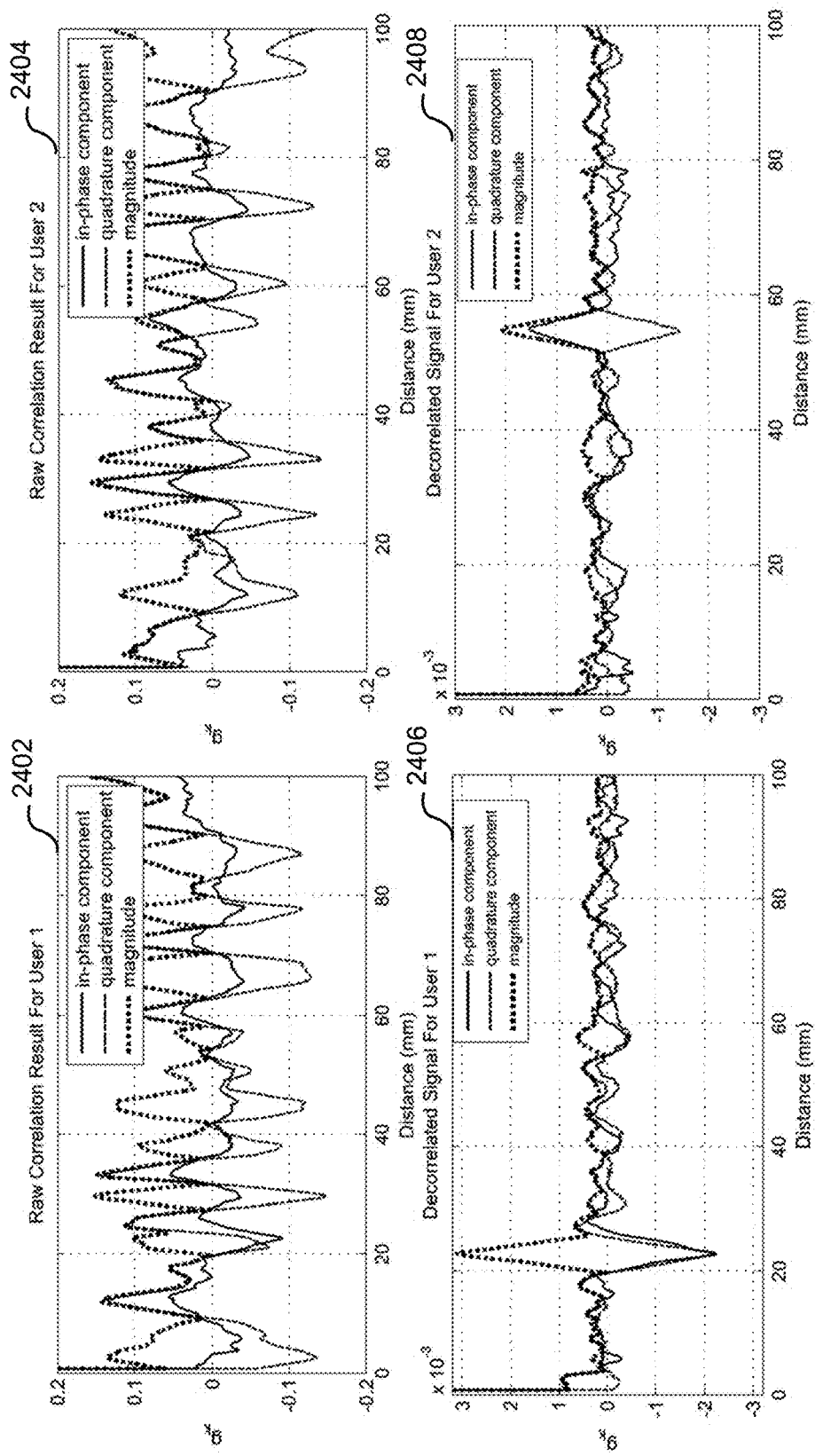
FIG. 24 depicts cross-correlation results before and after multi-user decorrelation.

FIG. 24 illustrates results during two different stages of retrieving the individual responses. The top row of results in the figure are plots 2402, 2404 of the first cross-correlation result. It appears as noise as it contains all the uncorrelated information as well as the correlated information for both users. The second row plots 2406, 2408 depicts the medium responses from each user after multi-user decorrelation is complete. Note that even though the scattered information for both scatterers was picked up at the common receiver, only the scatterer illuminated by the individual user's sequence shows up in their response. In other words the medium's response to a specific user is not detected in the other user's response. Each user's medium response, user, is unique to that user. Each user could have also illuminated both scatterers in which case both scatterers would appear in each of the user's responses.

Special Considerations

Figure 25:
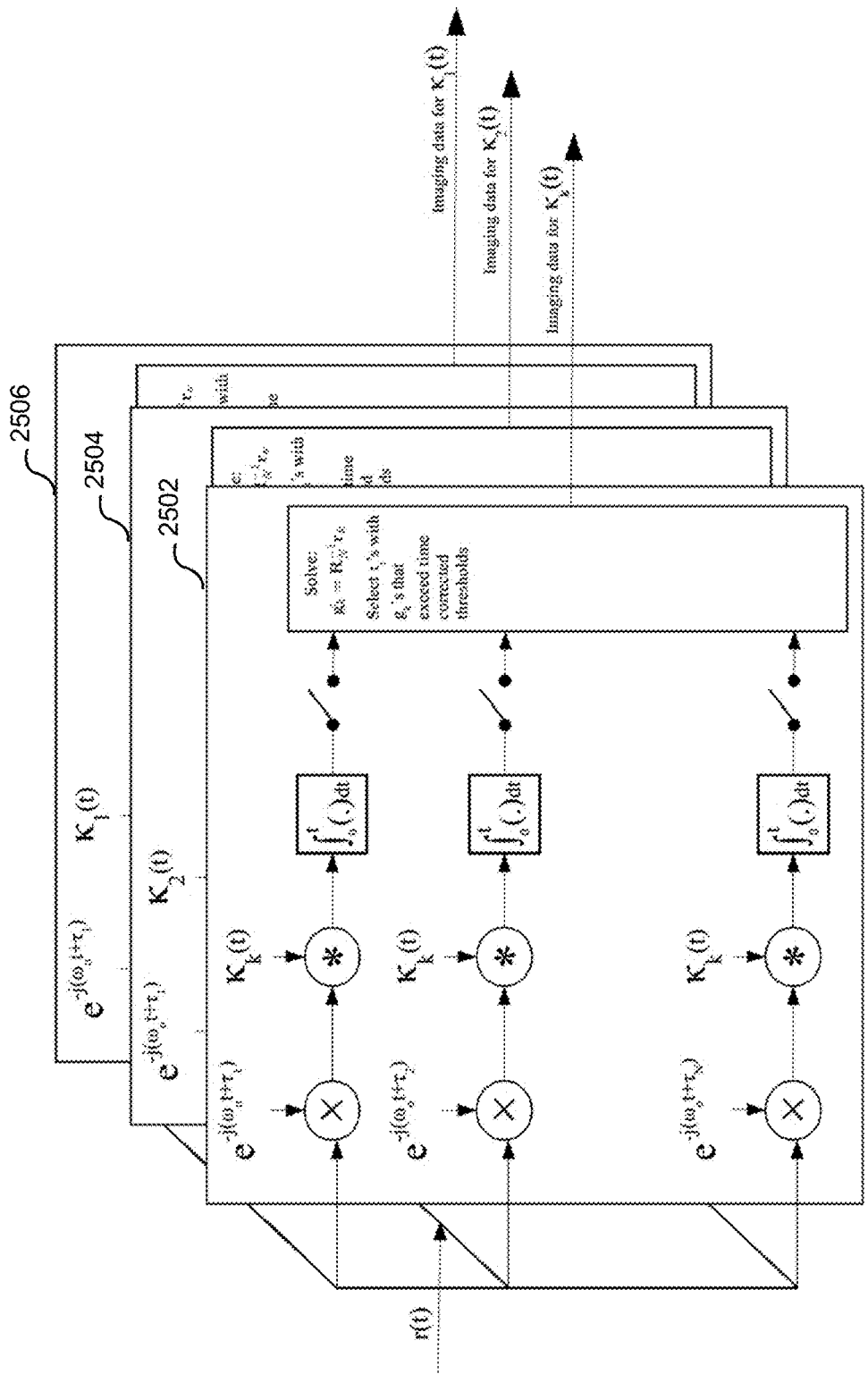
FIG. 25 depicts an asynchronous concurrent multi-excitation processing example.

Revisiting Equation (27) and modifying as shown below:

$$\hat{\Lambda}(g_x) = \int_0^{NT+2T} [r(t) - \Sigma_{k=1}^{K} \sqrt{\epsilon_k} \Sigma_{i=1}^{N} g(i)\kappa_x(t-iT-\tau_k)]^2 dt, x=1, \tag{27}$$

where the variable x separates the data for the multiple, unique asynchronous, concurrent excitations in a system. The identification of results at unknown values of $\tau_k$ are of interest for one signature sequence $\kappa_x$ because they identify sources of reflection at that time delay. FIG. 25 illustrates an example of the processing required for implementation of Equation (44) to provide decorrelation or multi-scan decorrelation. Decorrelation functions 2502, 2504, 2506 are utilized when there are multiple concurrent scanlines operating. Multi-scanline decorrelation is utilized to separate out the separate scan information that is be gathered concurrently.

For applications using different waves than the acoustic demonstration shown above and taking EM waves as an example, equation (45) with equations (46) and (47) would be used to replace equation (18). The main alteration is in the perturbation operator so that it reflects EM waves. Furthermore the parameters of interest that would be related to the in-phase and quadrature phase components would then be permittivity ($\epsilon$) and permeability ($\mu$), the parameters that affect EM waves.

$$\hat{g}_k(n) = \frac{1}{N\sigma_\kappa\sigma_r}\sum_{i=0}^{N-1}\kappa(n+i)r(n+iT) \quad (45)$$

$$= G_0(x_m, x_s)\delta(n-m) +$$

$$4\pi^2\left(\frac{1}{\lambda^2} - \frac{1}{\lambda_0^2}\right)G_0(x_n, x_s)\int_{\Omega_n} G_0(x_m, x')d\Omega(x')$$

$$\lambda = \frac{1}{f\sqrt{\epsilon\mu}} \quad (46)$$

$$G_0(x_m, x_n) = \frac{i}{4}H_0^1(2\pi f\sqrt{\epsilon\mu}|x_m - x_n|) \quad (47)$$

As described above, it is possible to image a medium or environment using a continuously transmitted signal and the received signals may be processed to provide a spatial mapping of the medium or environment. Various particular implementations are possible using the techniques described above, such as for example, an imaging system for non-destructive testing, imaging of objects, imaging of an environment etc. Depending upon the imaging signals used, it may be possible to provide imaging through other materials, which may allow imaging of for example construction materials or structures through building walls, or other coverings.

Figure 26:
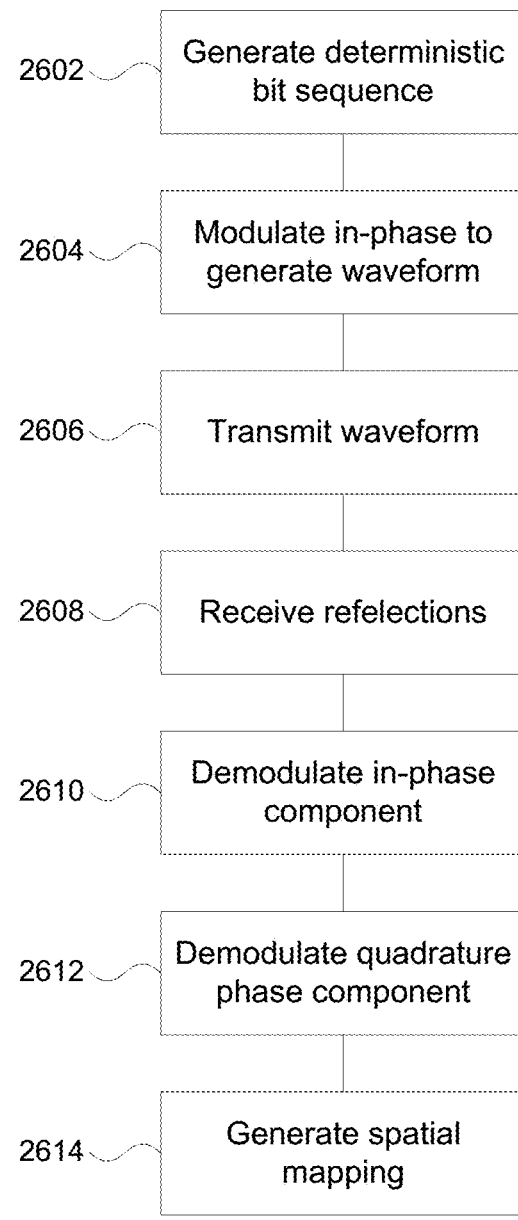
FIG. 26 depicts a method of imaging a medium using modulated excitation.

FIG. 26 depicts a method of imaging a medium using modulated excitation. A deterministic bit sequence is generated by a processor (2602), such for example a PN sequence or a Kasami sequence. The sequence is modulated in-phase to generate an imaging waveform (2604) which is transmitted by a transducer into the medium being imaged (2606). The transducer may be acoustic of electro-magnetic depending on the medium or environment being imaged. Response signals are received by the transducer associated reflected from the medium or environment based upon properties of the medium or environment (2608). In-phase demodulation the response signal (2610) and quadrature phase demodulation of the response signal (2612) are performed. The processor can then utilize the demodulated in-phase component of the response signal and the quadrature phase component of the response signal to create a spatial mapping of properties of the medium being imaged (2614) and apply multi-user deconvolution if multiple scanlines are in use. The processor can determine the composition of the medium and distance of anomalies or layers within the medium. A look-up table may be utilized to map the response signal to material and distance properties based upon the deterministic bit sequence utilized. The system may be utilized to generate a multi-scanline of the medium or environment. To utilize multi-scanlines a plurality of deterministic bit sequences can be generated and transmitted into the medium or environment by the transducer. The demodulated in-phase and quadrature phase components can be de-correlated based up each of the plurality of deterministic bit sequences to generate respective scan lines for generating the spatial mapping.

Figure 27:
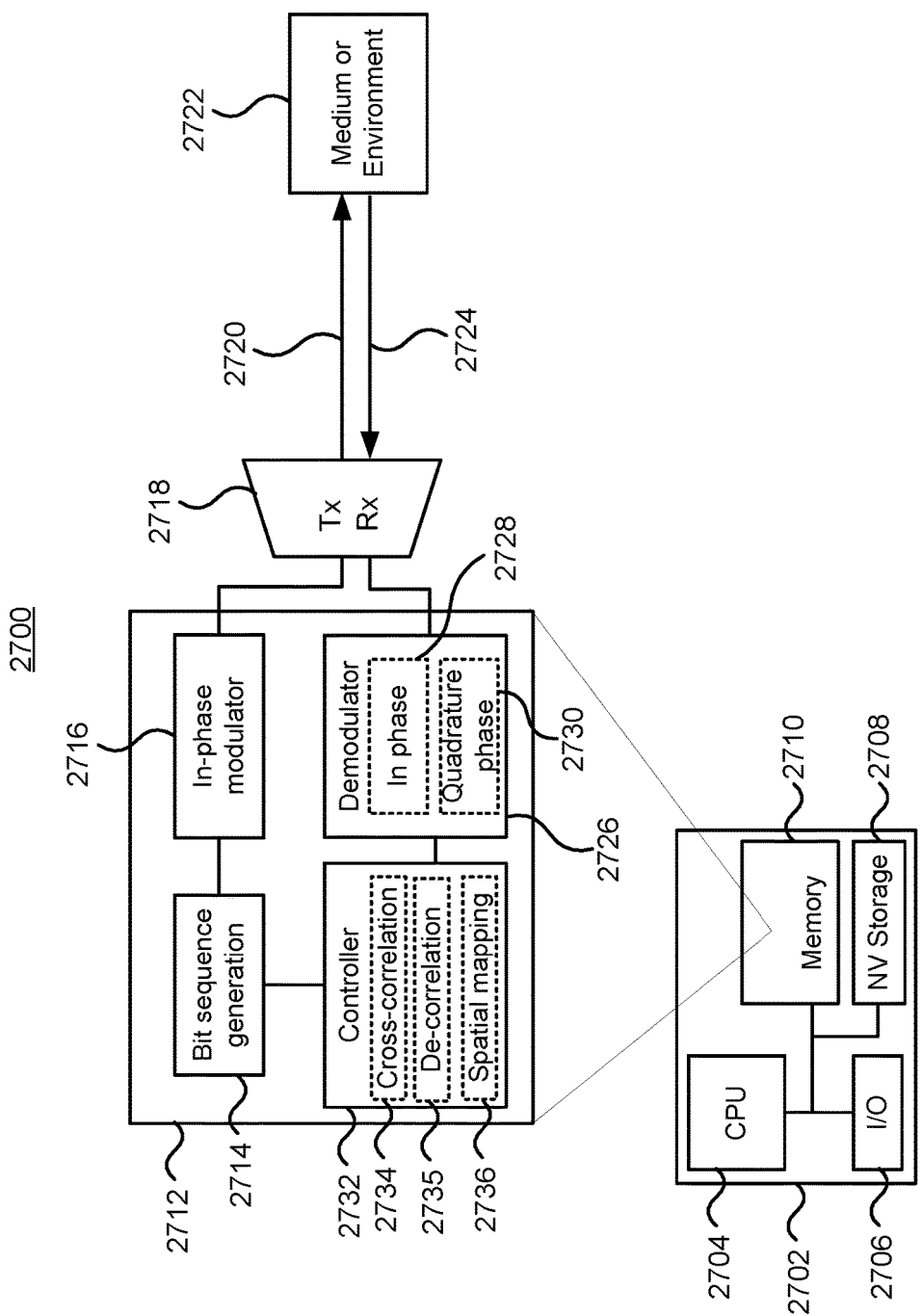
FIG. 27 depicts an imaging system.

FIG. 27 depicts an imaging system. The system 2700 comprises a computing device 2702 comprising a processor 2704 for executing instructions. The processor 2704 may be coupled to an input/output (I/O) interface 2706, for connecting other devices such as keyboards, touch sensors, displays, network interfaces, etc. The computing device 2702 may further include non-volatile (NV) storage 2708 and a memory unit 2710 for storing instructions, which may be executed by the processor 2704. The memory unit 2710 may store instructions, which when executed by the processor 2704 configure the computing device 2702 to provide imaging functionality 2712 implementing the imaging techniques described above.

The imaging functionality 2712 comprises bit sequence generating functionality 2714 that generates a bit sequence, for example a Kasami bit sequence. The generated bit sequence is provided to in-phase modulation functionality 2716 that modulates the bit sequence on a particular carrier frequency and outputs the generated waveform to a transducer 2718. The generated waveform is transmitted 2720 into the medium or environment and reflected by an anomaly or object 2722. The reflected wave 2724 is reflected back to the transducer 2718 where it is received and provided to demodulator functionality 2727 provided by the computing device 2702. The demodulator functionality 2726 comprises in-phase demodulation functionality 2728 and quadrature phase demodulation functionality 2730. The in-phase and quadrature demodulated components are provided to controller functionality 2732 for processing the demodulated components. The controller functionality 2732 includes cross-correlation functionality 2734 for cross-correlating the demodulated components with the generated bit sequences. De-correlation functionality 2735 can also be provided when multi-scan de-correlation is required. The correlated signals may then be processed by spatial mapping functionality 2336 that determines the spatial mapping based on for example equation (34). The generated spatial mapping may be displayed or used as desired.

Various specific details have been described above. While certain features or functionality may be described in particular detail with regard to one device or component, it will be appreciated that the functionality or features may be applied to other devices or components. Further, although various embodiments of the devices, equipment, functionality, etc. are described herein, the description is intended to provide an understanding of the systems, methods and devices and as such certain aspects may not be described, or not described in as much detail as other aspects. The described systems, methods and devices are not the sole possible implementations, and the various descriptions systems, methods and devices herein will enable one of ordinary skill in the art to apply the teachings to other equivalent implementations without exercising any inventive ingenuity.

Although certain components and steps have been described, it is contemplated that individually described components, as well as steps, may be combined together into fewer components or steps or the steps may be performed sequentially, non-sequentially or concurrently. Further, although described above as occurring in a particular order, one of ordinary skill in the art having regard to the current teachings will appreciate that the particular order of certain steps relative to other steps may be changed. Similarly, individual components or steps may be provided by a plurality of components or steps. One of ordinary skill in the art having regard to the current teachings will appreciate that the system and method described herein may be provided by various combinations of software, firmware and/or hardware, other than the specific implementations described herein as illustrative examples.

Some embodiments are directed to a computer program product comprising a computer-readable medium comprising code for causing a computer, or multiple computers, to implement various functions, steps, acts and/or operations, e.g. one or more or all of the steps described above. Depending on the embodiment, the computer program product can, and sometimes does, include different code for each step to be performed. Thus, the computer program product may, and sometimes does, include code for each individual step of a method, e.g., a method of operating a communications device, e.g., a wireless terminal or node. The code may be in the form of machine, e.g., computer, executable instructions stored on a non-transitory computer-readable medium such as a RAM (Random Access Memory), ROM (Read Only Memory) or other type of storage device. In addition to being directed to a computer program product, some embodiments are directed to a processor configured to implement one or more of the various functions, steps, acts and/or operations of one or more methods described above. Accordingly, some embodiments are directed to a processor, e.g., CPU, configured to implement some or all of the steps of the method(s) described herein. The processor may be for use in, e.g., a communications device or other device described in the present application.

Numerous additional variations on the methods and apparatus of the various embodiments described above will be apparent to those skilled in the art in view of the above description. Such variations are to be considered within the scope.

The invention claimed is:

1. An imaging system comprising:
a deterministic bit sequence generator for generating a deterministic transmit sequence;
an in-phase modulator for modulating the generated deterministic transmit sequence with a transmit carrier frequency to generate an imaging waveform;
a transducer for transmitting the generated imaging waveform into a medium or environment being imaged and receiving a response signal;
an in-phase demodulator for demodulating an in-phase component of the response signal;
a quadrature demodulator for demodulating a quadrature phase component of the response signal; and
a controller for processing the demodulated in-phase component of the response signal and the quadrature phase component of the response signal to create a spatial mapping of properties of the medium or environment being imaged from code offsets of the demodulated in-phase component, the demodulated quadrature phase component, and the deterministic transmit sequence.

2. The imaging system of claim 1, wherein the controller is configured to:
cross-correlate the response signal with the generated deterministic transmit sequence.

3. The imaging system of claim 1, wherein the generated deterministic transmit sequence is a Kasami sequence.

4. The imaging system of claim 1 wherein the deterministic bit sequence generator further generates a plurality of deterministic transmit sequences for generating a plurality of scanlines wherein the in-phase and quadrature phase components are de-correlated to generate the plurality of scanlines for each deterministic transmit sequence to generate the spatial mapping.

5. The imaging system of claim 1, further comprising:
a display controller for displaying a representation of the spatial mapping of the properties of the medium or environment being imaged.

6. The imaging system of claim 1, wherein the controller is configured to measure separately reflected energy amounts contained in the in-phase and quadrature phase components to spatially located and determine target composition.

7. The imaging system of claim 1, wherein the transducer is an ultrasonic transducer.

8. The imaging system of claim 1, wherein the transducer is an electromagnetic (EM) wave transducer.

9. The imaging system of claim 8 wherein the controller measures resulting power levels in the in-phase component and quadrature phase component to make determinations regarding the medium or environment.

10. The imaging system of claim 1, wherein the response signal is compared to a table of in-phase component value and quadrature component value for a pseudo-noise (PN) sequence to determine a distance and target composition in the medium or environment.

11. The imaging system of claim 1 wherein the deterministic transmit sequence comprises a pseudo-noise (PN) sequence that has an autocorrelation result that approximates an impulse function and has a cross correlation result with an optimum lower bound.

12. The imaging system of claim 1 wherein the deterministic transmit sequence is modulated on a specific carrier frequency and phase while demodulating on multiple phases and differing frequencies.

13. A method of imaging a medium, the method comprising:
generating a deterministic bit sequence by a bit sequence generator;
performing in-phase modulation of the generated deterministic bit sequence to generate an imaging waveform;
transmitting, by a transducer, the imaging waveform into the medium being imaged;
receiving a response signal by the transducer associated reflected from the medium;
performing in-phase demodulation of an in-phase component of the response signal;
performing quadrature phase demodulation of a quadrature phase component of the response signal; and
processing, by the processor controller, the demodulated in-phase component of the response signal and the demodulated quadrature phase component of the response signal to create a spatial mapping of properties of the medium being imaged from code offsets of the demodulated in-phase component, the demodulated quadrature phase component, and the deterministic bit sequence.

14. The method of claim 13, wherein the deterministic bit sequence is a Kasami sequence.

15. The method of claim 13, further comprising measuring separately reflected energy in the in-phase and quadrature phase components to spatially locate and determining target composition in the medium.

16. The method of claim 15 wherein resulting power levels are measured in the in-phase component and quadrature phase component to make determinations regarding the medium.

17. The method of claim 13, wherein the transducer is an ultrasonic transducer.

18. The method of claim 13, wherein the transducer is an electromagnetic (EM) wave transducer.

19. The method of claim 13, wherein the response signal is compared to a table of in-phase component value and quadrature component value for a pseudo-noise (PN) sequence to determine a distance and target composition in the medium.

20. The method of claim 13 wherein the deterministic bit sequence comprises a pseudo-noise (PN) sequence that has an autocorrelation result that approximates an impulse function and has a cross correlation result with an optimum lower bound.

21. The method of claim 13 wherein the imaging waveform is modulated on a specific carrier frequency and phase while the in-phase demodulation and quadrature phase modulation are performed on multiple phases and different frequencies.

22. The method of claim 13 wherein generating the deterministic bit sequence further comprises generating a plurality of deterministic bit sequences and wherein in-phase demodulation of in-phase components and quadrature phase demodulation of quadrature phase components are de-correlated based upon each of the plurality of deterministic bit sequences to generate respective scanlines for generating the spatial mapping.

\* \* \* \* \*